United States Patent [19]
Studt et al.

[11] Patent Number: 4,707,478
[45] Date of Patent: Nov. 17, 1987

[54] HETEROCYCLIC AMIDINO SUBSTITUTED UREAS AND THEIR PHARMACEUTICAL USES

[75] Inventors: William L. Studt, Harleysville; Harry K. Zimmerman, Quakertown; Stuart A. Dodson, Lansdale, all of Pa.

[73] Assignee: Rorer Pharmaceutical Corporation, Fort Washington, Pa.

[21] Appl. No.: 425,095

[22] PCT Filed: Aug. 24, 1981

[86] PCT No.: PCT/US81/01146
§ 371 Date: Sep. 16, 1982
§ 102(e) Date: Sep. 16, 1982

[87] PCT Pub. No.: WO83/00627
PCT Pub. Date: Mar. 3, 1983

[51] Int. Cl.$^4$ .................. A61K 31/17; A61K 31/55; A61K 31/47; A61K 31/44

[52] U.S. Cl. .................. 514/580; 514/277; 514/307; 514/311; 514/313; 514/344; 514/396; 514/408; 514/461; 514/588; 514/553

[58] Field of Search .............. 514/277, 344, 580, 588, 514/553, 307, 311, 313, 408, 461, 396

[56] References Cited

U.S. PATENT DOCUMENTS

| | | | |
|---|---|---|---|
| 3,539,616 | 11/1970 | Walls | 260/465 |
| 3,798,269 | 3/1974 | Cutler et al. | 260/553 |
| 3,933,794 | 1/1976 | Hester, Jr. et al. | 260/239 BD |
| 3,984,467 | 10/1976 | Diana | 260/553 A |
| 4,009,163 | 2/1977 | Cutler et al. | 260/247.2 A |
| 4,025,652 | 5/1977 | Diamond et al. | 514/580 |
| 4,058,557 | 11/1977 | Douglas et al. | 260/501.14 |
| 4,060,635 | 11/1977 | Diamond et al. | 514/520 |
| 4,088,785 | 5/1978 | Diamond et al. | 514/580 |
| 4,115,564 | 9/1979 | Diamond et al. | 514/212 |
| 4,163,022 | 7/1979 | Diamond | 260/553 R |
| 4,166,860 | 9/1979 | Douglas et al. | 514/400 |
| 4,169,155 | 9/1979 | Douglas et al. | 514/596 |
| 4,178,387 | 12/1979 | Diamond et al. | 514/596 |
| 4,220,658 | 9/1985 | Douglas et al. | 514/277 |
| 4,225,315 | 9/1980 | Won et al. | 23/230 PC |
| 4,241,087 | 12/1980 | Mir et al. | 514/211 |
| 4,304,786 | 12/1981 | Diamond et al. | 514/277 |
| 4,340,609 | 7/1982 | Chou | 514/595 |
| 4,486,439 | 12/1984 | Studt et al. | 514/357 |

FOREIGN PATENT DOCUMENTS 0012361 6/1980 European Pat. Off.
53-108970 9/1978 Japan.

OTHER PUBLICATIONS

Medicinal Chem., 2nd Ed., Interscience Pubs. Inc., N.Y., 1960.
Chem. Abst., 98:185594m, 1983.
Chem. Abst., 98:160594y, 1983.
Chem. Abst., 98:160595z, 1983.
Black, J. W. et al, "Definition and Antagonism of Histamine $H_2$-Receptors", Nature, vol. 236, Apr. 1972.
Chemical Abstracts 94:84174m.
Curd et al, "Synthetic Antimalarials, Part XLII, The Preparation of Guanylureas and Biurets Corresponding to Paludrine and Related Biguanides", J. Chem. Soc., p. 1732 (1949).
Skowronska-Serafin, B. & Urbanski, T., "Preparation of Derivatives of Amidineurea and Their Reactions," Tetrahedron, vol. 10, pp. 12-24 (1960).
Goodford et al, "Predictions of the Anitmalarial Activity of Arylamidinoureas", Brit, J. Pharmacol, vol. 48, pp. 650-654 (1973).
Bredereck et al, "Reaction of Formamide with Acetone in the Gas Phase", Chemical Abstracts, vol. 51, No. 11, Nov. 10, 1957, pp. 16420-f-i to 16421-a-c.
Douglas et al, Arzneimittel Forschung (Drug Research), 28(II), pp. 1433-1480 (1978).
Szlompeck-Nesteruk et al, "Derivatives of Aminopyrazine and Its N-Oxides, I. Synthesis and Spectra", Rocz. Chem. 1973, 47(11), 2127-2139, [Chem. Abstracts, vol. 80, 1974, p. 408, 95882c.].
Chemical Abstracts, vol. 90, No. 11, Mar. 12, 1979, p. 608, Abstract No. 87298F.
Beisler, "Isolation, Characterization, and Properties of a Labile Hydrolysis Product of the Antitumor Nucleoside, 5-Azacytodine", Journal of Medicinal Chemistry, 1978, vol. 21, No. 2, pp. 204-208.

Primary Examiner—Johnnie R. Brown
Assistant Examiner—John W. Rollins, Jr.
Attorney, Agent, or Firm—James A. Nicholson; Alexis Barron; Martin F. Savitzky

[57] ABSTRACT

This invention relates to methods for the prophylactic and curative treatment of gastrointestinal and cardiovascular disorders and parasitic infections in humans and animals, using a class of hetrocyclic amidino substituted urea and thiourea compounds, a novel class of heterocyclic amidino substituted urea and thiourea compounds and pharmaceutical compositions and animal feed additives including the same.

4 Claims, No Drawings

HETEROCYCLIC AMIDINO SUBSTITUTED UREAS AND THEIR PHARMACEUTICAL USES

FIELD OF THE INVENTION

This invention relates to a novel class of heterocyclic amidino substituted ureas and thioureas and their pharmaceutical use in methods for producing gastrointestinal, cardiovascular, and antiparasitic action, among others.

REPORTED DEVELOPMENTS

Phenylamidinoureas and their uses as antisecretory, antispasmodic, anti-ulcerogenic, anesthetic and antidiarrheal agents have been reported in *Arzneimittel Forschung* (Drug Research) 28 (II), 1433–1480 (1978), and U.S. Pat. Nos. 4,025,652, 4,058,557, 4,060,635, 4,088,785, 4,115,564, 4,115,647, 4,117,165, 4,147,804, 4,150,154, 4,169,155, 4,178,387, 4,204,000 and 4,220,658.

This invention relates to a class of heterocyclic amidino substituted urea and thiourea compounds which also possess valuable pharmaceutical properties.

SUMMARY OF THE INVENTION

This invention relates to the treatment of humans and animals afflicted with gastrointestinal disorders, spasmolytic disorders, ulcergenic disorders, cardiovascular disorders, diarrheal disorders, and parasitic infestations with compositions containing an effective amount of heterocylic amidino substituted urea or thiourea according to Formula I

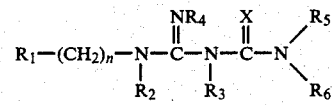

where:
- X is O or S;
- n is 0 to 3;
- $R_1$ is a 5 to 7 atom ring or a 7 to 13 atom fused or bridged ring which may include 1 to 4 hetero atoms of N, O or S; and containing a total of about 3 to about 20 carbon atoms; and the N- or S-oxides thereof;
- $R_2$, $R_3$ and $R_4$ are hydrogen or lower alkyl;
- $R_5$ and $R_6$ are hydrogen, alkyl, cycloalkyl, aralkyl, aryl, alkenyl, alkoxy or a heterocyclic group, or $R_5$ and $R_6$ together with the nitrogens to which they are attached form a 3 to 7 atom ring which may include 0 to 2 additional hetero atoms of N, O or S; and the nontoxic acid addition salts thereof.

DETAILED DESCRIPTION OF THE INVENTION

This invention also relates to novel compounds which are useful in these methods and include those according to Formula I where:
- n is 0, 1, 2 or 3;
- $R_1$ is a substituted or unsubstituted 5, 6 or 7 atom ring including 1 to 3 hetero atoms of N, O or S; and N- and S-oxides thereof;
- $R_2$ is hydrogen or lower alkyl;
- $R_3$ and $R_4$ are hydrogen;
- $R_5$ and $R_6$ are hydrogen, lower alkyl, lower alkenyl, cycloalkyl, lower alkoxy, or aralkyl or $R_5$ and $R_6$ together with the nitrogen to which they are attached form a 3 to 7 atom heterocycle.

This invention further relates to a novel class of compounds according to Formula I, which are useful in the above methods, in which $R_1$ is one of the following heterocylic groups: 1-pyrrole, 2-pyrrole, 3-pyrrole, 2-furan, 3-furan, 2-thiophene, 3-thiophene, 2-tetrahydrothiophene, 3-tetrahydrothiophene, 2-imidazole, 2-imidazole, 4-imidazole, 5-imidazole, 2-oxazole, 4-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 1-(3-pyrroline), 2-(3-pyrroline), 3-(3-pyrroline), 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, or carbazole.

The heterocylic groups above may be mono-, di-, tri- or tetra-substituted by ring substituents, such as, halogen, lower alkyl, lower alkenyl, aryl, lower alkynyl, aralkyl, nitro, cyano, sulfonyl, hydroxyl, carboxyl, lower alkanoyl, lower alkoxy, aryl lower alkoxy, halo lower alkoxy, amido, amino, lower alkyl acyloxy, alkylamino, lower alkoxyamino, and aralkoxyamino.

A preferred embodiment of this invention is a compound according to Formulae II–IV

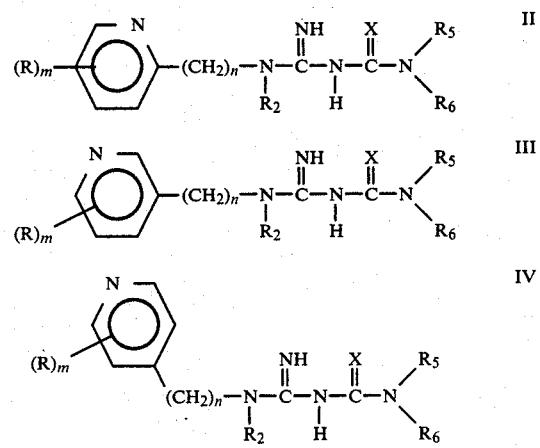

- m is zero to four;
- n is zero, one, two or three;
- R represents a ring substituent as described above, and the N-oxides of the pyridyl nitrogen atom; and
- $R_2$, $R_5$ and $R_6$ are as described in Formula I above.

Another preferred embodiment of this invention is a compound according to Formula V or VI

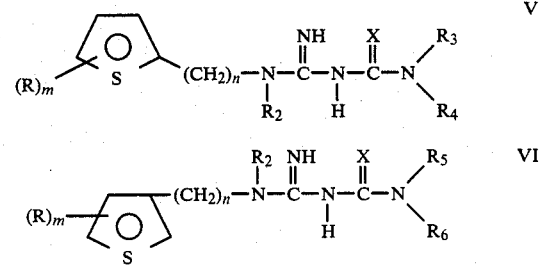

where:

m is zero to three n is zero, one, two or three;

R represents a ring substituent as described above; and the S-oxides of the thiophene sulfur atoms, such as, thiophenylsulfoxide and thiophenyl sulfone;

$R_2$, $R_5$ and $R_6$ are as defined above in Formula I; and the nontoxic acid addition salts thereof.

A particularly preferred embodiment of this invention is a compound according to Formula II, III, IV, V and VI, wherein X, m, n, R, and $R_2$ are as described above, and one of $R_5$ and $R_6$ are phenyl or substituted phenyl. The most preferred substituted phenyl groups are those which are ortho- and diortho-substituted.

In any discussion of the true structure of an amidinourea, tautomerism must be considered. It should be clear to anyone skilled in the art that the amidinourea chain can be legitimately represented in any one of several tautomeric forms. When the amidinourea is in solution, one form may predominate over another depending upon the degree and location of substitution and on the nature of the solvent. The rates of conversion of one tautomer to another will depend upon the nature of the solvent, the degree of hydrogen bonding permitted, the temperature, and possibly other factors (such as pH, trace impurities and the like).

To illustrate what is meant by this, a number of likely structures are here shown for just one of the compounds of this invention:

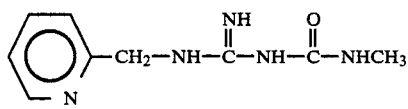

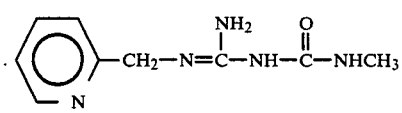

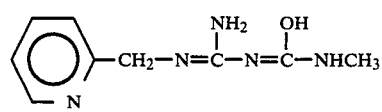

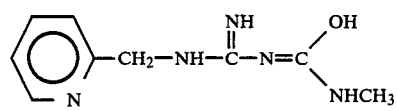

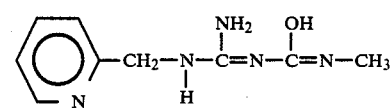

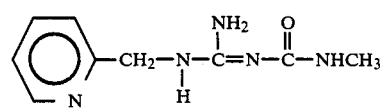

Of course, other structures are possible, such as those with hydrogen bonding.

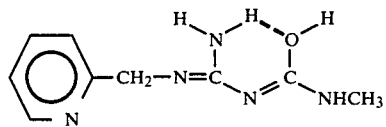

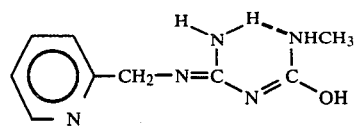

Furthermore, the heterocylic atom may contribute to structures reflecting hydrogen bonding.

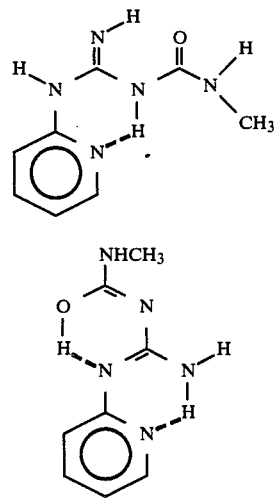

As employed above and throughout the disclosure, the following terms, unless otherwise indicated, shall be understood to have the following meanings:

"Alkyl" means a saturated aliphatic hydrocarbon which may be either straight- or branched-chain. Preferred groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" means an alkyl group as above, having 1 to 6 carbon atoms. Suitable lower alkyl groups are methyl, ethyl, n-propyl, isopropyl, butyl, sec-butyl, tert-butyl, n-pentyl, isopentyl and neopentyl.

"Cycloalkyl" means an aliphatic monocyclic saturated carbocyclic group having 3 to 6 carbon atoms. Preferred groups are cyclopropyl, cyclopentyl and cyclohexyl.

"Alkenyl" means an unsaturated aliphatic hydrocarbon. Preferred groups have no more than about 12 carbon atoms and 1 to 3 carbon double bonds and may include straight or branched chains, and may be any structural and geometric isomers of ethenyl, propylenyl, butenyl, pentenyl, hexenyl, heptenyl, octenyl, nonenyl, decenyl, undecenyl, and dodecenyl or butadienyl, pentadienyl etc. Also included are the cycloalkylene groups such as cyclopropenyl, cyclopentenyl, cyclohexenyl, etc. and the cycloalkylalkylene groups such as cyclo-propyleneylmethyl, and cyclohexenylmethyl and the like.

"Lower alkenyl" means alkenyl or 2 to 6 carbon atoms such ethylene, propylene, butylene, isobutylene, etc., including all structural and geometrical isomers thereof.

"Alkynyl" means an unsaturated aliphatic hydrocarbon. Preferred groups have no more than about 12 carbon atoms and contain one or more triple bonds, including any structural or geometric isomers or acetylenyl, propynyl, butynyl, pentynyl, hexynyl, heptynyl, octynyl, nonynyl, decynyl, undecynyl, dodecynyl, etc.

"Lower alkynyl" means alkynyl of 2 to 6 carbon atoms such as structural and geometric isomers of propargyl, butynyl, pentynyl, etc.

"Aryl" means phenyl and substituted phenyl.

"Substituted phenyl" means a phenyl group in which one or more of the hydrogens has been replaced by the same or different substituents including halo, lower alkyl, halo-lower alkyl, nitro, amino, acylamino, hydroxyl, lower alkoxy, aryl lower alkoxy, acyloxy, cyano, halo-lower alkoxy or lower alkyl sulfonyl. The preferred substituted phenyl group is phenyl in which the 2 and 6 positions are substituted.

"Aralkyl" means an alkyl (preferably a lower alkyl) in which one or more hydrogens is substituted by an aryl moiety (preferably phenyl or substituted phenyl), e.g., benzyl, phenethyl, etc.

"Heterocyclic group" or "heterocycle" means a 3, 5, 6 or 7 membered ring having 1 to 3 hetero atoms which may be nitrogen, oxygen or sulfur, including pyridyl, pyrimidyl, pyrazolyl, imidazolyl, furyl, thienyl, oxazolyl, thiazolyl, piperidyl, morpholinyl, oxazolidinyl, thiazolidinyl, pyrazolodinyl, imidazolidinyl, piperazinyl, thiamorpholinyl, trimethylenetriaminyl and ethyleneiminyl; where the heterocycle may be mono-, di-, tri- or tetra-substituted by lower alkyl, lower alkenyl, lower alkynyl, aryl, aralkyl, halo, nitro, cyano, sulfonyl, hydroxyl, carboxyl, lower alkanoyl, lowercarboalkoxy, lower alkoxy, aryl lower alkoxy, halo lower alkoxy, amido, amino, lower alkylamino, aralkylamino, lower alkoxyamino, and aralkylamino.

"Substituted heterocycle" means a heterocycle in which one or more of the hydrogens on the ring carbons have been replaced by substituents as given above with respect to substituted phenyl.

The terms "halo" and "halogen" include all four halogens; namely, fluorine, chlorine, bromine and iodine. The halo alkyls, halophenyl and halo-substituted pyridyl include groups having more than one halosubstituent which may be the same or different such as trifluoromethyl, 1-chloro-2-bromo-ethyl, chlorophenyl, 4-chloropyridyl, etc.

"Acyloxy" means an organic acid radical of a lower alkanoic acid or aromatic acid such as acetoxy, propionoxy, benzoyloxy, and the like.

"Acyl" means an organic radical of the formula RCO where R is alkyl or aromatic, such as, lower alkanoyl and aroyl. Exemplary acyl groups are acetyl, benzoyl, napthoyl, etc.

"Lower alkanoyl" means the acyl radical of a lower alkanoic acid such as acetyl, propionyl, butyryl, valeryl, stearoyl, and the like.

"Alkoxy" is intended to include hydroxy alkyl groups, preferably lower alkyl groups such as methoxy, ethoxy, n-propoxy, i-propoxy, and the like.

The preferred "aralkyl" groups are benzyl and phenethyl.

The preferred "halo lower alkyl" group is trifluoromethyl.

The preferred "halo lower alkoxy" group is trifluoromethoxy.

It is well known in the pharmacological arts that nontoxic acid addition salts of pharmacologically active amine compounds do not differ in activities from their free base. The salts merely provide a convenient solubility factor.

The amidinoureas of this invention may be readily converted to their nontoxic acid addition salts by customary methods in the art. The nontoxic salts of this invention are formed from the base amidinourea and an acid which is pharmacologically acceptable in the intended dosages. Such salts would include those prepared from inorganic acids, organic acids, higher fatty acids, high molecular weight acids, etc. Exemplary acids are hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, etc.

Representative examples of the compounds of this invention are listed in Tables I and II.

The nomenclature used in the tables below and which apply to the compounds of this invention is as follows:

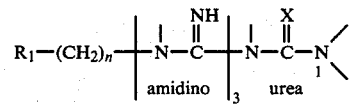

It should be understood that alternate nomenclature can be used to adequately describe the compounds of this invention, one such system of nomenclature being based on the quanidine structure,

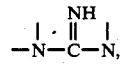

and which system is used in the preparative example section below.

TABLE I 3-(2-pyridylamidino)-1-methylurea
3-(2-pyridylamidino)-1-ethylurea
3-(2-pyridylamidino)-1-propylurea
3-(2-pyridylamidino)-1-i-propylurea
3-(2-pyridylamidino)-1-butylurea
3-(2-pyridylamidino)-1-i-butylurea
3-(2-pyridylamidino)-1-pentylurea
3-(2-pyridylamidino)-1-propargylurea
3-(2-pyridylamidino)-1-allylurea
3-(2-pyridylamidino)-1-methoxyethylurea
3-(2-pyridylamidino)-1-benzyloxyethylurea
3-(2-pyridylamidino)-1-phenethoxyethylurea
3-(2-pyridylamidino)-1-(N,N-dimethyl)urea
3-(2-pyridylamidino)-1-(N,N-diethyl)urea
3-(2-pyridylamidino)-1-(N,N-tetramethylene)urea
3-(2-pyridylamidino)-1-(N,N-pentamethylene)urea
3-(2-pyridylamidino)-1-(N,N-hexamethylene)urea
3-(2-[3-methylpyridyl]amidino)-1-methylurea
3-(2-[3-methylpyridyl]amidino)-1-ethylurea
3-(2-[3-methylpyridyl]amidino)-1-propylurea
3-(2-[3-methylpyridyl]amidino)-1-i-propylurea
3-(2-[3-methylpyridyl]amidino)-1-i-butylurea 3-(2-[3-methylpyridyl]amidino)-1-pentylurea
3-(2-[3-methylpyridyl]amidino)-1-allylurea
3-(2-[3-methylpyridyl]amidino)-1-propargylurea
3-(2-[3-methylpyridyl]amidino)-1-cyclopropylurea
3-(2-[3-methylpryidyl]amidino)-1-methoxyethylurea
3-(2-[3-methylpyridyl]amidino)-1-benzyloxyethylurea
3-(2-[3-methylpyridyl]amidino)-1-phenethoxyethylurea
3-(2-[3-methylpyridyl]amidino)-1-benzylurea
3-(2-[3-methylpyridyl]amidino)-1-(N,N-dimethyl)urea
3-(2-[3-methylpyridyl]amidino)-1-(N,N-diethyl)urea
3-(2-[3-methylpyridyl]amidino)-1-(N,N-tetramethylene)urea
3-(2-[3-methylpyridyl]amidino)-1-(N,N-pentamethylene)urea
3-(2-[3-chloropyridyl]amidino)-1-methylurea
3-(2-[3-chloropyridyl]amidino)-1-ethylurea
3-(2-[3-chloropyridyl]amidino)-1-propylurea
3-(2-[3-chloropyridyl]amidino)-1-i-propylurea
3-(2-[3-chloropyridyl]amidino)-1-butylurea
3-(2-[3-chloropyridyl]amidino)-1-i-butylurea
3-(2-[3-chloropyridyl]amidino)-1-t-butylurea
3-(2-[3-chloropyridyl]amidino)-1-pentylurea
3-(2-[3-chloropyridyl]amidino)-1-allylurea
3-(2-[3-chloropyridyl]amidino)-1-propargylurea
3-(2-[3-chloropyridyl]amidino)-1-cyclopropylurea
3-(2-[3-chloropyridyl]amidino)-1-cyclobutylurea
3-(2-[3-chloropyridyl]amidino)-1-(N-[3'-cyclopentenyl])urea
3-(2-[3-chloropyridyl]amidino)-1-cyclopropylmethylurea
3-(2-[3-chloropyridyl]amidino)-1-methoxyethylurea
3-(2-[3-chloropyridyl]amidino)-1-benzyloxyethylurea
3-(2-[3-chloropyridyl]amidino)-1-phenethoxyethylurea
3-(2-[3-chloropyridyl]amidino)-1-benzylurea
3-(2-[3-chloropyridyl]amidino)-1-(N,N-dimethyl)urea
3-(2-[3-chloropyridyl]amidino)-1-(N,N-diethyl)urea
3-(2-[3-chloropyridyl]amidino)-1-(N,N-tetramethylene)urea
3-(2-pyridylamidino)-1-(N,N[3'-methyl-3'-azapentamethylene]urea
3-(2-pyridylamidino)-1-(N,N[3'-oxapentamethylene]urea
3-(3-pyridylamidino)-1-methylurea
3-(3-pyridylamidino)-1-ethylurea
3-(3-pyridylamidino)-1-propylurea
3-(3-pyridylamidino)-1-propylurea
3-(3-pyridylamidino-1-butylurea
3-(3-pyridylamidino)-1-i-butylurea
3-(3-pyridylamidino)-1-t-butylurea
3-(3-pyridylamidino)-1-pentylurea
3-(3-pyridylamidino)-1-allylurea
3-(3-pyridylamidino)-1-propargylurea
3-(3-pyridylamidino)-1-cyclobutylurea
3-(3-pyridylamidino)-1-cyclohexylurea
3-(3-pyridylamidino)-1-benzylurea
3-(3-pyridylamidino)-1-methoxyethylurea
3-(3-pyridylamidino)-1-benzyloxyethylurea
3-(3-pyridylamidino)-1-methoxyethylurea
3-(3-pyridylamidino)-1-benzyloxyethylurea
3-(3-pyridylamidino)-1-phenethoxyethylurea
3-(3-pyridylamidino)-1-(N,N-diethyl)urea
3-(3-pyridylamidino)-1-(N,N-dimethyl)urea
3-(3-pyridylamidino)-1-(N,N-pentamethylene)urea
3-(4-pyridylamidino)-1-methylurea
3-(4-pyridylamidino)-1-ethylurea
3-(4-pyridylamidino)-1-propylurea
3-(4-pyridylamidino)-1-i-propylurea
3-(4-pyridylamidino)-1-butylurea
3-(4-pyridylamidino)-1-t-butylurea
3-(4-pyridylamidino)-1-pentylurea
3-(4-pyridylamidino)-1-hexylurea
3-(4-pyridylamidino)-1-propargylurea
3-(4-pyridylamidino)-1-allylurea
3-(4-pyridylamidino)-1-methoxyethylurea
3-(4-pyridylamidino)-1-benzyloxyethylurea
3-(4-pyridylamidino)-1-phenethoxyethylurea
3-(4-pyridylamidino)-1-(N,N-dimethyl-urea
3-(4-pyridylamidino)-1-(N,N-diethyl)urea
3-(4-pyridylamidino)-1-(N-methyl-N-ethyl)urea
3-(4-pyridylamidino)-1-(N,N-tetramethylene)urea
3-(4-pyridylamidino)-1-(N,N-pentamethylene)urea
3-(4-pyridylamidino)-1-(N,N-hexamethylene)urea
3-(4-[2-ethylpyridyl]amidino)-1-methylurea
3-(4-[2-ethylpyridyl]amidino)-1-ethylurea
3-(4-[2-ethylpyridyl]amidino)-1-propylurea
3-(4-[2-ethylpyridyl]amidino)-1-butylurea
3-(4-[2-ethylpyridyl]amidino)-1-i-butylurea
3-(4-[2-ethylpyridyl]amidino)-1-pentylurea
3-(4-[2-ethylpyridyl]amidino)-1-allylurea
3-(4-[2-ethylpyridyl]amidino)-1-propargylurea
3-(4-[2-ethylpyridyl]amidino)-1-methoxyethylurea
3-(4-[2-ethylpyridyl]amidino)-1-benzyloxyethylurea
3-(4-[2-ethylpyridyl]amidino)-1-(N,N-dimethyl)urea
3-(4-[2-ethylpyridyl]amidino)-1-(N,N-diethyl)urea
3-(4-[2-ethylpyridyl]amidino)-1-(N,N-tetramethylene)urea
3-(4-[2,6-dichloropyridyl]amidino)-1-methylurea
3-(4-[2,6-dimethylpyridyl]amidino)-1-methylurea
3-(4-[2-methyl,6-chloropyridyl]amidino)-1-methylurea
3-(2-thiophenylamidino)-1-methylurea
3-(3-thiophenylamidino)-1-methylurea
3-(2-[5-methylthiophenyl]amidino)-1-methylurea
3-(2-[5-chlorothiophenyl]amidino)-3-methylurea
3-(2-pyridyl-N-oxideamidino)-1-(N,N-dimethyl)urea
3-(2-[3-cyanopyridyl]amidino)-1-methylurea
3-(2-[3-carbomethoxypyridyl]amidino)-1-methylurea
3-(2-[3-carboethoxypyridyl]amidino)-1-methylurea
3-(2-[6-chloropyridyl]amidino)-1-methylurea
3-(2-[6-methylpyridyl]amidino)-1-methylurea
3-(2-[3-ethylpyridyl]amidino)-1-methylurea
3-(3-[2-methylpyridyl]amidino)-1-methylurea
3-(3-[2-ethylpyridyl]amidino)-1-methylurea
3-(3-[2,6-dimethylpyridyl]amidino)-1-methylurea
3-(2-[3-cyanothiophenyl]amidino)-1-methylurea
3-(2-[3-carbomethoxythiophenyl]amidino)-1-methylurea
3-(2-[3-carboethoxythiophenyl]amidino)-1-methylurea
3-(3-[2-methoxypyridyl]amidino)-1-methylurea
3-(3-[2-ethoxypyridyl]amidino)-1-methylurea
3-(3-[2-chloropyridyl]amidino)-1-methylurea
1-(2-furylamidino)urea
1-(3-furylamidino)urea
1-(2-[3-methylfuryl]amidino)urea
3-furylamidino-1-ethylurea
3-(2-furylamidino)-1-propylurea
3-(2-furylamidino)-1-i-propylurea
3-(2-furylamidino)-1-butylurea
3-(2-furylamidino)-1-i-butylurea
3-(2-furylamidino)-1-sec-butylurea
3-(2-furylamidino)-1-t-butylurea
3-(2-furylamidino)-1-pentylurea
3-(2-furylamidino)-1-hexylurea
3-(2-furylamidino)-1-heptylurea
3-(2-furylamidino)-1-cyclopropylurea
3-(2-furylamidino)-1-cyclobutylurea
3-(2-pyridyl-N-oxideamidino)-1-methylurea 3-(2-pyridyl-N-oxideamidino)-1-methylurea
3-(4-pyridyl-N-oxideamidino)-1-methylurea
3-(2-furylamidino)-1-methylurea
3-(3-furylamidino)-1-methylurea
3-(2-tetrahydrofurylamidino)-1-methylurea
3-(3-tetrahydrofurylamidino)-1-methylurea
3-(1-imidazoalamidino)-1-methylurea
3-(2-imidazoalamidino)-1-methylurea
3-(4-imidazoalamidino)-1-methylurea
3-(2-oxazoalamidino)-1-methylurea
3-(4-oxazoalamidino)-1-methylurea
3-(5-oxazoalamidino)-1-methylurea
3-(2-thiazoalamidino)-1-methylurea
3-(4-thiazoalamidino)-1-methylurea
3-(5-thiazoalamidino)-1-methylurea
3-(1-pyrazoalamidino)-1-methylurea
3-(1-[3-pyrrolino]amidino)-1-methylurea
3-(2-pyrrolinoamidino)-1-methylurea
3-(1-morpholinoamidino)-1-methylurea
3-(2-morpholinoamidino)-1-methylurea
3-(2-pyrimidinoamidino)-1-methylurea
3-(4-pyrimidinoamidino)-1-methylurea
3-(2-quinolinoamidino)-1-methylurea
3-(4-quinolinoamidino)-1-methylurea
3-(1-isoquinolinoamidino)-1-methylurea
3-(2-furylamidino)-1-cyclopentylurea
3-(2-furylamidino)-1-cyclohexylurea
3-(2-furylamidino)-1-phenylurea
3-(2-furylamidino)-1-benzylurea
3-(2-furylamidino)-1-phenethylurea
3-(2-furylamidino)-1-(N-methyl-N-benzyl)urea
3-(2-furylamidino)-1-(N,N-dibenzyl)urea
1-(2-tetrahydrofurylamidino)urea
1-(2-[3-methyltetrahydrofuryl]amidino)urea
1-(3-tetrahydrofurylamidino)urea
1-(3-[2-methyltetrahydrofuryl]amidino)urea
1-(1-imidazoalamidino)urea
1-(1-[2-methylimidazoal]amidino)urea
1-(4-imidazoalamidino)urea
1-(4-[1-methylimidazoal]amidino)urea
1-(4-[2-methylimidazoal]amidino)urea
1-(2-imidazoalamidino)urea
1-(2-oxazoalamidino)urea
1-(2-[4-methyloxazoal]amidino)urea
1-(4-oxazoalamidino)urea
1-(4-[2-methyloxazoal]amidino)urea
1-(5-oxazoalamidino)urea
1-(5-[2-methyloxazoal]amidino)urea
1-(4-thiazoalamidino)urea
1-(4-[5-methylthiazoal]amidino)urea
1-(5-thiazoalamidino)urea
1-(5-[4-methylthiazoal]amidino)urea
1-(1-pyrazoalamidino)urea
1-(1-[3-pyrrolino]amidino)urea
1-(2-[3-pyrrolino]amidino)urea
1-(1-[2-methyl-3-pyrrolino]amidino)urea
1-(1-[3-methyl-2-pyrrolino]amidino)urea
1-(1-pyrrolidinoamidino)urea
1-(1-[2-methylpyrrolidino]amidino)urea
1-(2-pyrrolidinoamidino)urea
1-(2-[1-methylpyrrolidino]amidino)urea
1-(1-morpholinoamidino)urea
1-(1-[2-methylmorpholino]amidino)urea
1-(2-morpholinoamidino)urea
1-(2-[1-methylmorpholino]amidino)urea
1-(2-[3-methylmorpholino]amidino)urea
1-(1-[3-methylmorpholino]amidino)urea
1-(3-morpholinoamidino)urea
1-(3-[1-methylmorpholino]amidino)urea
1-(3-[2-methylmorpholino]amidino)urea
1-(2-pyrimidinoamidino)urea
1-(2-[4-methylpryimidino]amidino)urea
1-(4-pyrimidinoamidino)urea
1-(4-[2-methylpyrimidino]amidino)urea
1-(2-quinolinoamidino)urea
1-(2-[3-methylquinolino]amidino)urea
1-(4-quinolinoamidino)urea
1-(4-[2-methylquinolino]amidino)urea
1-(4-[3-methylquinolino]amidino)urea
1-(1-isoquinolinoamidino)urea TABLE 1-a $$R_a-NHC(=NH)-NHC(=O)-N(R_5)(R_6)$$

| $R_a$ | $R_5$ | $R_6$ |
|---|---|---|
| 2,4-dichloropyridin-3-yl | H | —CH₃ |
| 2,4-dichloropyridin-3-yl | H | —C₂H₅ |
| 3-chlorothien-2-yl | H | —CH₃ |
| 3-chlorothien-2-yl | H | —C₂H₅ |
| 3,5-dimethylthien-4-yl | H | —CH₃ |
| 3,5-dimethylthien-4-yl | H | —C₂H₅ |
| 3-methyl-5-chloro-4-methylthien-... | H | —CH₃ |

TABLE 1-a-continued $$R_a\text{—NHC(=NH)—NHC(=O)—N(R_5)(R_6)}$$

| $R_a$ | $R_5$ | $R_6$ |
|---|---|---|
| 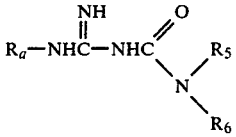 (2-furyl) | H | —CH₃ |
|  (2-furyl) | H | H |
|  (3-furyl) | H | —CH₃ |
| 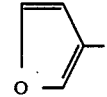 (3-furyl) | H | —C₂H₅ |
|  (2-thienyl) | H | —CH₃ |
| 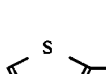 (2-thienyl) | —CH₃ | —CH₃ |
| 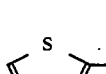 (N-methylpyrrolyl) | —H | —CH₃ |
| 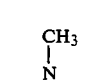 (N-methylpyrrolyl) | —H | —C₂H₅ |
| 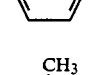 (isoxazolyl) | —H | —CH₃ |
| 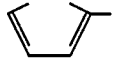 (dimethylpyrazinyl) | —CH₃ | —CH₃ |
| 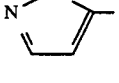 (dimethylpyrazinyl) | H | —C₂H₅ |
| 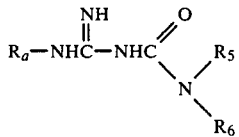 (4-pyridyl) | H | H |
| 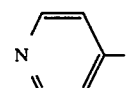 (4-pyridyl) | H | —CH₃ |
|  (imidazolyl) | H | H |
| 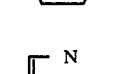 (imidazolyl) | H | —CH₃ |
| 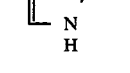 (imidazolyl) | H | —C₂H₅ |
| 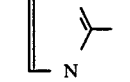 (pyrazolyl) | H | H |
|  (pyrazolyl) | H | —CH₃ |
| 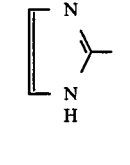 (dimethylpyridyl) | H | H |
| 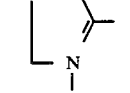 (dimethylpyridyl) | H | —CH₃ |

TABLE 1-a-continued $$R_a-NHC(=NH)-NHC(=O)-N(R_5)(R_6)$$

| $R_a$ | $R_5$ | $R_6$ |
|---|---|---|
| 4-CH₃, 2-CH₃-pyridin-3-yl | H | —C₂H₅ |
| 3,5-(CH₃)₂-pyridin-4-yl | H | —OCH₃ |
| 3,5-(CH₃)₂-pyridin-4-yl | —CH₃ | —CH₃ |
| 3,5-(CH₃)₂-pyridin-4-yl | —CH₃ | —C₂H₅ |
| 2-C₂H₅-pyridin-3-yl | H | H |
| 2-C₂H₅-pyridin-3-yl | H | —CH₃ |
| 2-C₂H₅-pyridin-3-yl | H | —C₂H₅ |
| 4-CH₃, 2-CH₃-pyridin-3-yl-CH₂ | H | H |
| 4-CH₃, 2-CH₃-pyridin-3-yl-CH₂ | H | —CH₃ |
| 4-CH₃, 2-CH₃-pyridin-3-yl-CH₂ | H | —C₂H₅ |
| 4-CH₃, 2-CH₃-pyridin-3-yl-CH₂ | H | —OCH₃ |
| 3,5-(CH₃)₂-pyridin-4-yl-CH₂ | —CH₃ | —CH₃ |
| 3,5-(CH₃)₂-pyridin-4-yl-CH₂ | —CH₃ | —C₂H₅ |
| 2-CH₃-pyridin-3-yl-CH₂ | H | H |
| 2-CH₃-pyridin-3-yl-CH₂ | H | —CH₃ |
| 2-CH₃-pyridin-3-yl-CH₂ | H | —C₂H₅ |
| furan-2-yl-CH₂— | H | —CH₃ |

TABLE 1-a-continued
$$R_a-NHC(=NH)-NHC(=O)-N(R_5)(R_6)$$
| $R_a$ | $R_5$ | $R_6$ |
|---|---|---|
| 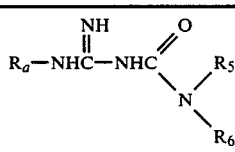 | H | H |
| 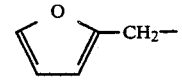 | H | —CH₃ |
| 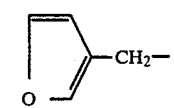 | H | —C₂H₅ |
|  | H | —CH₃ |
| 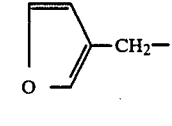 | —CH₃ | —CH₃ |
| 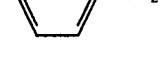 | —H | —CH₃ |
| 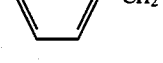 | —H | —C₂H₅ |
| 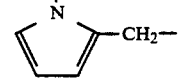 | —H | —CH₃ |
| 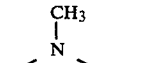 | H | H |
| 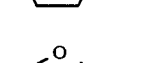 | H | —CH₃ |
| 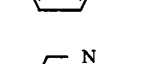 | —CH₃ | —CH₃ |
| 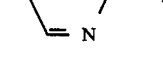 | —H | —CH₃ |
| 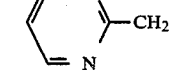 | —H | —C₂H₅ |
| 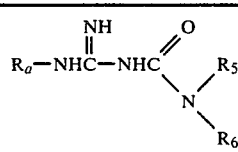 | —CH₃ | —CH₃ |
| 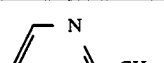 | H | H |
| 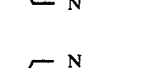 | H | —CH₃ |
| 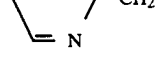 | —CH₃ | —CH₃ |
| 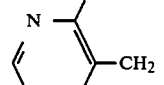 | H | —C₂H₅ |
| 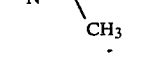 | H | H |
| 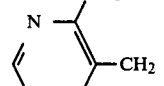 | H | —CH₃ |
| 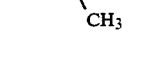 | H | H |

TABLE 1-a-continued
$$R_a-NHC\overset{\overset{NH}{\|}}{-}NH\overset{\overset{O}{\|}}{C}-\overset{R_5}{\underset{R_6}{N}}$$
| $R_a$ | $R_5$ | $R_6$ |
|---|---|---|
| 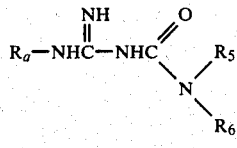 | H | —CH$_3$ |
| 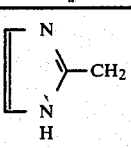 | H | —C$_2$H$_5$ |
| 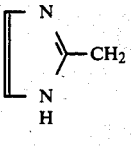 | H | H |
| 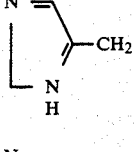 | H | —CH$_3$ |
| 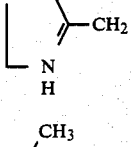 | H | H |
| 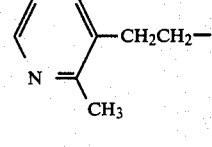 | H | —CH$_3$ |
| 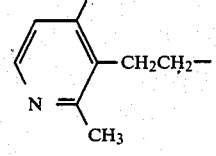 | H | —C$_2$H$_5$ |
| 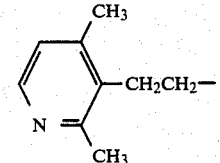 | H | —OCH$_3$ |
| 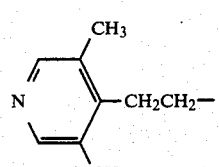 | —CH$_3$ | —CH$_3$ |
| 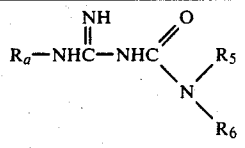 | —CH$_3$ | —C$_2$H$_5$ |
| 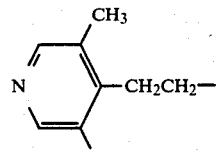 | H | H |
| 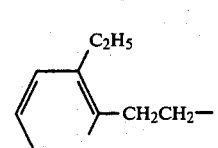 | H | —CH$_3$ |
| 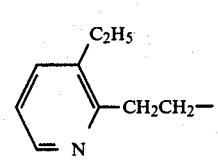 | H | —C$_2$H$_5$ |
| 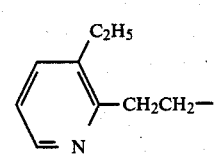 | H | H |
| 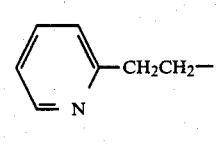 | H | —CH$_3$ |
| 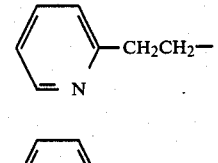 | H | —C$_2$H$_5$ |
| 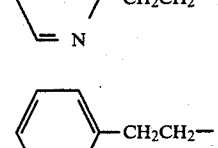 | —CH$_3$ | —CH$_3$ |
| 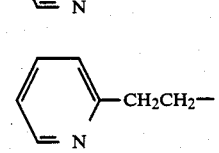 | H | —OCH$_3$ |
| 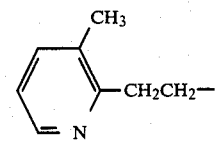 | H | —CH$_3$ |

TABLE 1-a-continued $$R_a-NHC(=NH)-NHC(=O)-N(R_5)(R_6)$$

| $R_a$ | $R_5$ | $R_6$ |
|---|---|---|
| 3-methyl-pyridin-2-yl-CH₂CH₂– | –CH₃ | –CH₃ |
| 3-methyl-pyridin-2-yl-CH₂CH₂– | –C₂H₅ | –C₂H₅ |
| 4,6-dimethyl-pyrimidin-5-yl-CH₂CH₂– | –CH₃ | –CH₃ |
| 4,6-dimethyl-pyrimidin-5-yl-CH₂CH₂– | H | –C₂H₅ |
| pyridin-4-yl-CH₂CH₂– | H | H |
| pyridin-4-yl-CH₂CH₂– | H | –CH₃ |
| imidazol-2-yl-CH₂CH₂– | H | H |
| imidazol-2-yl-CH₂CH₂– | H | –CH₃ |
| imidazol-2-yl-CH₂CH₂– | H | –C₂H₅ |
| imidazol-4-yl-CH₂CH₂– | H | H |
| imidazol-4-yl-CH₂CH₂– | H | –CH₃ |
| pyridin-2-yl-CH₂CH₂– | H | H |
| pyridin-2-yl-CH₂CH₂– | H | –CH₃ |
| pyridin-2-yl-CH₂CH₂– | –CH₃ | –CH₃ |
| pyridin-2-yl-CH₂CH₂– | –H | –CH₃ |
| pyridin-2-yl-CH₂CH₂– | –H | –C₂H₅ |
| pyridin-2-yl-CH₂CH₂– | –CH₃ | –CH₃ |
| 4,6-dimethyl-pyrimidin-5-yl-CH₂CH₂– | H | H |
| 4,6-dimethyl-pyrimidin-5-yl-CH₂CH₂– | H | –CH₃ |
| furan-2-yl-CH₂-CH₂– | H | –CH₃ |
| furan-2-yl-CH₂-CH₂– | H | H |

TABLE 1-a-continued $$R_a-NHC(=NH)-NHC(=O)-N(R_5)(R_6)$$

| $R_a$ | $R_5$ | $R_6$ |
|---|---|---|
| 3-furyl-CH₂-CH₂- | H | —CH₃ |
| 3-furyl-CH₂-CH₂- | H | —C₂H₅ |
| 2-thienyl-CH₂-CH₂- | H | —CH₃ |
| 2-thienyl-CH₂-CH₂- | —CH₃ | —CH₃ |
| 1-methyl-2-pyrrolyl-CH₂-CH₂- | —H | —CH₃ |
| 1-methyl-2-pyrrolyl-CH₂-CH₂- | —H | —C₂H₅ |
| 5-isoxazolyl-CH₂-CH₂- | —H | —CH₃ |
| 2-pyrimidinyl- | H | H |
| 2-pyrimidinyl- | H | —CH₃ |
| 2-pyrimidinyl- | —CH₃ | —CH₃ |
| 2-pyrimidinyl- | —H | —CH₃ |
| 2-pyrimidinyl- | —H | —C₂H₅ |
| 2-pyrimidinyl- | —CH₃ | —CH₃ |
| 4,5,6-trimethyl-2-pyrimidinyl- | H | H |
| 4,5,6-trimethyl-2-pyrimidinyl- | H | —CH₃ |
| 5-isothiazolyl- | H | —C₂H₅ |
| 2-pyridyl- | H | H |
| 2-pyridyl- | H | —CH₃ |
| 2-pyridyl- | H | —C₂H₅ |
| 2-pyridyl- | —CH₃ | —CH₃ |
| 2-pyridyl- | H | —OCH₃ |
| 3-methyl-2-pyridyl- | H | —CH₃ |

TABLE 1-a-continued $$R_a\text{—NHC(=NH)—NHC(=O)—N}R_5R_6$$

| $R_a$ | $R_5$ | $R_6$ |
|---|---|---|
| 2-methyl-3-methylpyridine (3-CH₃, 2-CH₂-pyridine via ring attach) | —CH₃ | —CH₃ |
| 3-methylpyridin-2-yl | —C₂H₅ | —C₂H₅ |
| 5-methylisothiazol-3-yl | H | —CH₃ |
| pyridin-2-ylmethyl | H | H |
| pyridin-2-ylmethyl | H | —CH₃ |
| pyridin-2-ylmethyl | H | —C₂H₅ |
| pyridin-2-ylmethyl | —CH₃ | —CH₃ |
| pyridin-2-ylmethyl | H | —OCH₃ |
| 3-methylpyridin-2-ylmethyl | H | —CH₃ |
| 3-methylpyridin-2-ylmethyl | —CH₃ | —CH₃ |
| 3-methylpyridin-2-ylmethyl | —C₂H₅ | —C₂H₅ |
| isoxazol-5-yl (5-methylisoxazol-3-yl) | H | —C₂H₅ |
| 3,5-dichloropyridin-4-ylmethyl | H | —CH₃ |
| 3,5-dichloropyridin-4-ylmethyl | H | —C₂H₅ |
| 3-chlorothien-2-ylmethyl | H | —CH₃ |
| 3-chlorothien-2-ylmethyl | H | —C₂H₅ |
| 3,4,5-trimethylthien-2-ylmethyl | H | —CH₃ |
| 3,4,5-trimethylthien-2-ylmethyl | H | —C₂H₅ |
| 5-chloro-3,4-dimethylthien-2-ylmethyl | H | —CH₃ |
| 5-chloro-3,4-dimethylthien-2-ylmethyl | H | —C₂H₅ |
| 4-methylisothiazol-5-ylmethyl | H | —CH₃ |

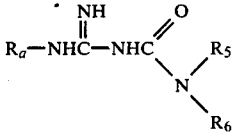

TABLE 1-a-continued
$$R_a-NHC(=NH)-NHC(=O)-N(R_5)(R_6)$$
| $R_a$ | $R_5$ | $R_6$ |
|---|---|---|
| 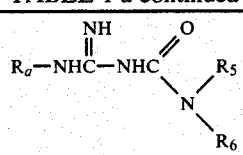 | H | —C$_2$H$_5$ |
| 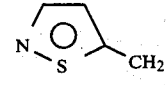 | —CH$_3$ | H |
| 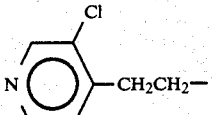 | —C$_2$H$_5$ | H |
| 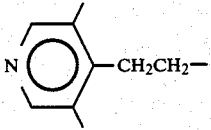 | —CH$_3$ | H |
| 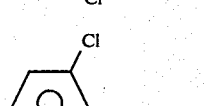 | —C$_2$H$_5$ | H |
| 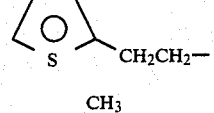 | —CH$_3$ | H |
| 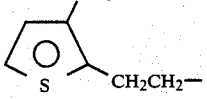 | —C$_2$H$_5$ | H |
| 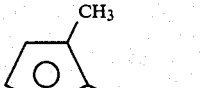 | —CH$_3$ | H |
| 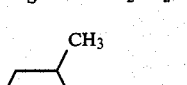 | —C$_2$H$_5$ | H |
| 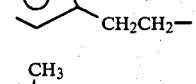 | —CH$_3$ | H |
| 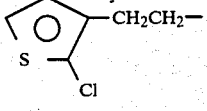 | —C$_2$H$_5$ | H |
TABLE 1-a-continued
$$R_a-NHC(=NH)-NHC(=O)-N(R_5)(R_6)$$
| $R_a$ | $R_5$ | $R_6$ |
|---|---|---|
| 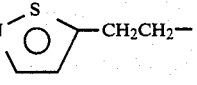 | H | 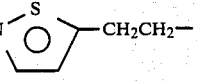 |
| 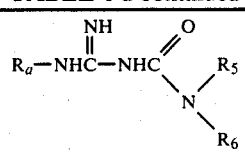 | H | 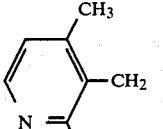 |
| 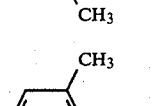 | H | 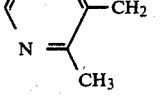 |
| 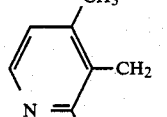 | H | 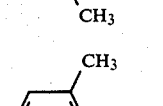 |
| 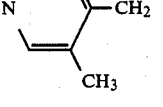 | —CH$_3$ | 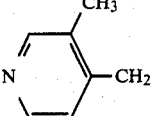 |
| 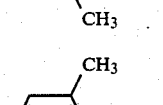 | —CH$_3$ | 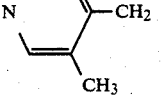 |
| 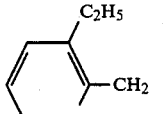 | H | 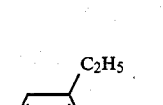 |
| 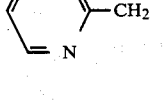 | H | Br, CH$_3$ substituted phenyl |

TABLE 1-a-continued $$R_a\text{—NHC(=NH)—NHC(=O)—N}R_5R_6$$

| $R_a$ | $R_5$ | $R_6$ |
|---|---|---|
| 3-ethyl-2-pyridylmethyl | H | 2,6-dimethylphenyl |
| 4,6-dimethylpyrimidin-5-yl | —CH$_3$ | 2,6-dimethylphenyl |
| 4,6-dimethylpyrimidin-5-yl | H | 2,6-dichlorophenyl |
| 4-pyridyl | H | 2-chloro-6-methylphenyl |
| 4-pyridyl | H | 2-chlorophenyl |
| 2-imidazolyl (NH) | H | 2-bromo-6-methylphenyl |
| 2-imidazolyl (NH) | H | 2-bromo-6-chlorophenyl |
| 2-imidazolyl (NH) | H | phenyl |
| 2-imidazolyl (NH) | H | 2-bromo-6-methylphenyl |
| 2-imidazolyl (NH) | H | 2,6-dimethylphenyl |
| 2-furyl | H | 2,6-dimethylphenyl |
| 2-furyl | H | 2,6-dichlorophenyl |
| 3-furyl | H | 2-chloro-5-methylphenyl |
| 3-furyl | H | 2-chlorophenyl |
| 2-thienyl | H | 2-bromo-6-methylphenyl |
| 2-thienyl | —CH$_3$ | 2-bromo-6-chlorophenyl |

TABLE 1-a-continued $$R_a-NHC(=NH)-NHC(=O)-N(R_5)(R_6)$$

| $R_a$ | $R_5$ | $R_6$ |
|---|---|---|
| 1-methylpyrrol-2-yl | —H | phenyl |
| 1-methylpyrrol-2-yl | —H | 4-bromophenyl (Br at 3-position) |
| isoxazol-5-yl | —H | 2,5-dimethylphenyl |
| 3,5-dimethylpyridin-4-yl (2,4-dimethyl) | H | 2,5-dimethylphenyl |
| 3,5-dimethylpyridin-4-yl | H | 2,6-dichlorophenyl |
| 3,5-dimethylpyridin-4-yl | H | 2-chloro-5-methylphenyl |
| 3,5-dimethylpyridin-4-yl | H | 2-chlorophenyl |
| 3,5-dimethylpyridin-4-yl | —CH$_3$ | 3-bromo-5-methylphenyl |
| 3,5-dimethylpyridin-4-yl | —CH$_3$ | 2-bromo-5-chlorophenyl |
| 3-ethylpyridin-2-yl | H | phenyl |
| 3-ethylpyridin-2-yl | H | 2-bromo-5-methylphenyl |
| 3-ethylpyridin-2-yl | H | 2,5-dimethylphenyl |

The compounds of this invention may be prepared by the following general synthesis:

Condensation of cyanamide and a heterocyclic amine results in the corresponding heterocyclic substituted guanidine.

The reaction is preferably carried out on the amino heterocyclic salt either in a polar medium or neat and using increased temperatures. The salt used may be any acid addition amine salt but preferably the salt of a mineral acid. The polar medium may be aqueous, partially aqueous or a non-aqueous solution. It is convenient to choose a solvent that will reflux at the desired reaction temperature. The more preferred solvents are water or alcohol but other solvents may be used such as DMSO, diethyleneglycol, ethyleneglycol, tetrahydrofuran, dimethylformamide, etc. The most preferred solvent is a mildly acidic solvent which is non-nucleophilic such as phenol, cresol, xylenol, etc. The reaction should also be carried out at a temperature which is high enough so that condensation takes place readily, but not sufficient to decompose the guanidine formed. The reaction temperature can vary from room temperature to about 250° C. although it is preferable to run the reaction at temperatures from about 50° C. to 150° C. The guanidine salt which is formed can be converted to the free base with a metal hydroxide or alkoxide solution. The isolation of the desired guanidine can be carried out by any method known in the art.

When the heterocyclic guanidine is reacted with a substituted isocyanate of the formula R'NCO, then the product formed is a 1-substituted heterocyclic amidino-3-R'-urea. This reaction is preferably carried out in a non-protic medium using solvents such as benzene, toluene, xylene, THF, etc. The reaction may be conducted at room temperature or as above at raised temperatures.

The following reaction equations illustrate this synthesis using 2-pyridyl as an exemplary heterocycle:

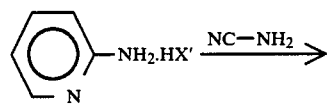

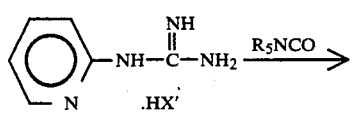

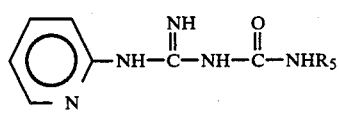

where: HX' is a mineral acid and $R_5$ is other than hydrogen.

When R substitution is desired in the $R_2$-position, it is convenient to carry out the condensation using the appropriately N-substituted heterocycle. Thus, for example, 2-pyridyl-N-methylamine would result in the 1-(2-pyridyl)-1-methyl-quanidine. This is then reacted as above with the isocyanate to form the amidinourea.

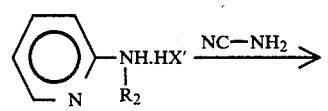

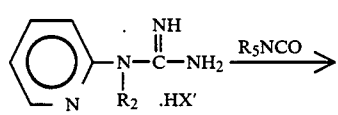

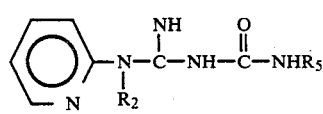

It is convenient to use t-butylisocyanate in the above reaction where substitution is not desired in the $R_3$-position. This may then be selectively hydrolyzed off.

When substitution is desired in the $R_3$ or $R_4$-position, it is convenient to carry out the condensation using the appropriately substituted cyanamide of the formula $NCNHR_3$. Thus, for example, methylcyanamide condensed with 2-pyridylamine would result in the corresponding 1-(2-pyridyl)-3-methylguanidine. This is then reacted as above with the isocyanate to form the amidinoureas.

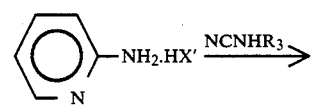

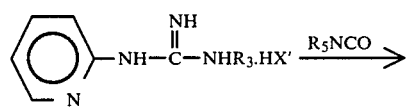

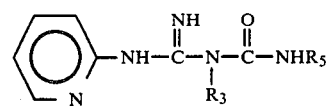

+

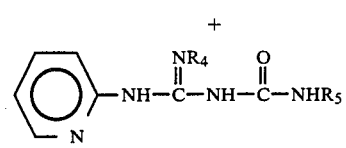

Condensation of a heterocyclic amine with benzoylthiourea results in the 1-heterocycle-3-benzoylthiourea. This may then be hydrolyzed to the 1-heterocycle thiourea and treated with iodomethane to obtain the 1-heterocyclic-2-methyl-pseudothiouronium iodide. When the latter is treated with an amine of the formula $NH_2R_3$, the resulting product is a 1-heterocyclic-3-R-guanidine which may then be reacted as above to form the amidinourea.

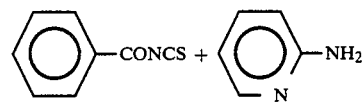

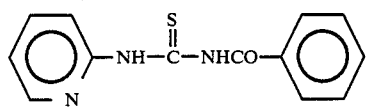

10% NaOH

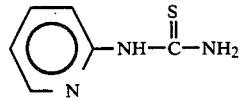

CH₃I

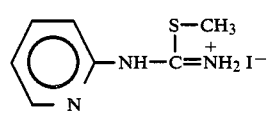

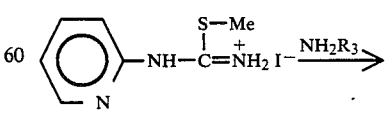

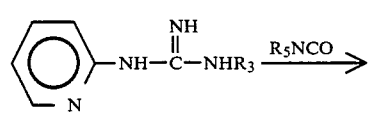

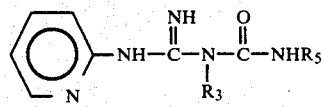

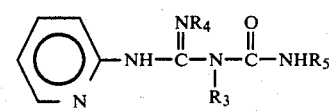

These compounds may also be prepared by condensing the desired amino heterocycle with a substituted isothiourea. The resulting guanidine compounds are reacted with an isocyanate as above to obtain the amidinourea.

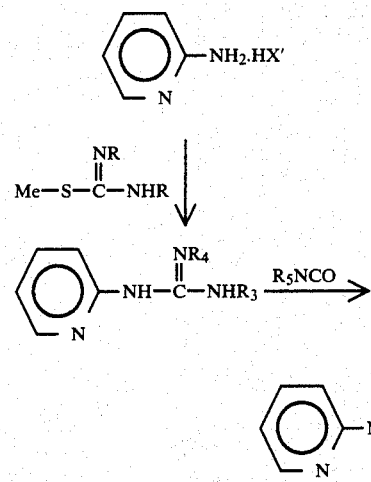

The heterocyclic amine may also be condensed with a thiocyanate of the formula SCNR. The reaction product is a thiourea which is then treated with iodomethane and reacted with an amine of the formula $NH_2R$ to obtain the desired guanidine.

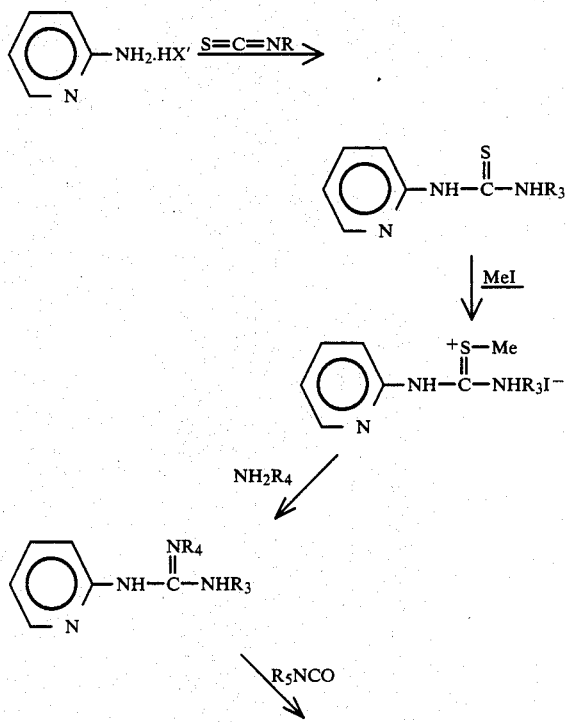

When substitution is desired in the $R_4$-position, the heterocyclic amine is condensed with t-butyl thiocyanate (SCN-t-butyl) to form the thiourea. The t-butyl group is then hydrolyzed off with conc. HCl. The product is reacted with an isocyanate to obtain the carbamylthiourea, which is treated with iodomethane and reacted with an amine of the formula $NHR_4$ to obtain the desired amidinourea.

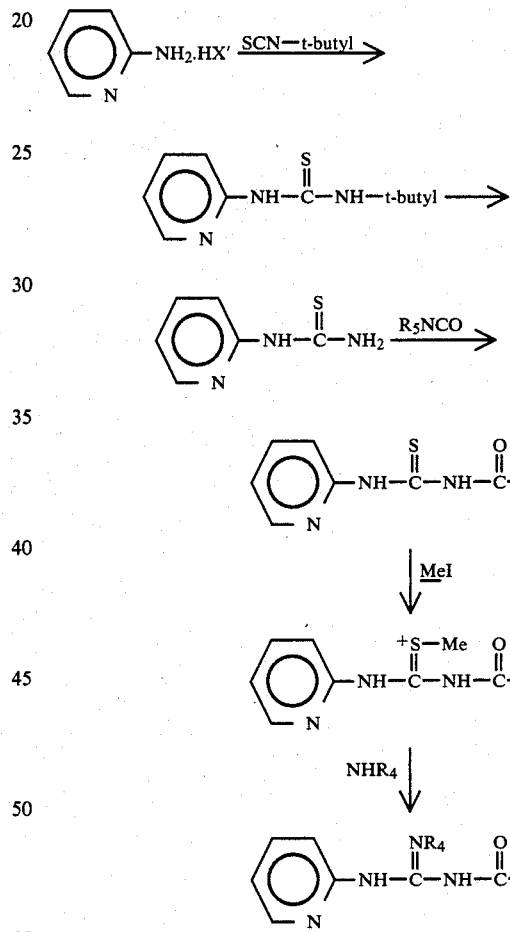

When $R_5$ and $R_6$ substitution is desired the appropriate guanidine is reacted with an acid chloride of the amine of the formula

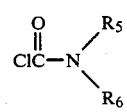

The latter is made by the reaction of the amine of the formula

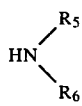

with phosgene in an inert solvent. The reaction of the acid chloride and guanidine is carried out in a polar medium and inert conditions at moderate temperatures.

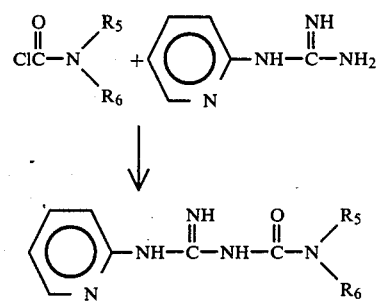

When substitution in the $R_5$ and $R_6$ positions is not desired, the desired heterocyclic amidinourea may be prepared by the acid hydrolysis of the 1-(heterocyclic)-3-cyano guanidine.

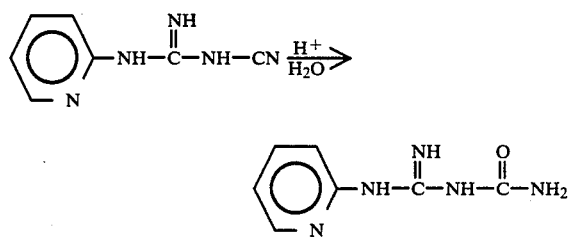

The cyano guanidine may be prepared by the reaction of the amino heterocycle with an N-cyano-O-$R_L$-psuedourea.

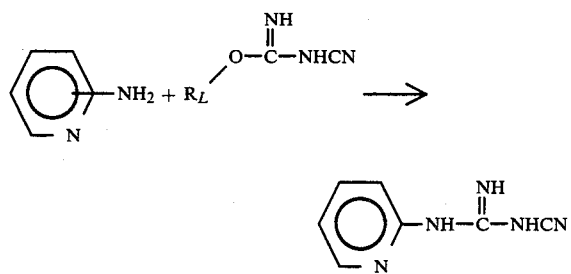

$R_L$ represents a suitable leaving group, such as a substituted phenyl group.

Appropriately desired end products having various $R_2$, $R_3$, $R_4$, $R_5$ and $R_6$ substituents may be prepared at various steps of synthesis using suitable reactions in order to convert one group to another.

The starting heterocyclic primary amines are either known, or may be prepared by known techniques. Thus, chlorination or bromination of a primary or secondary heterocyclic substituted amine may be carried out in acetic acid, or in the presence of a small amount of iodine dissolved in an inert solvent such as carbon tetrachloride. A solution of chlorine or bromine is then added while the temperature is held near 0° C. Iodination may also be carried out by known methods using iodine monochloride (ClI).

Alkylation may be carried out on an amine using an alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonium fluoroborate which is then thermally decomposed to the fluoro compound. Diazotization followed by a Sandmeyer type reaction may yield the bromo, chloro or iodo compound.

A chloro, bromo or iodo compound may also be reacted with trifluoromethyliodide and copper powder at about 150° C. in dimethylformamide to obtain a trifluoromethyl compound [Tetrahedron Letters: 47, 4095 (1959)].

A halo compound may also be reacted with cuprous methanesulfinate in quinoline at about 150° C. to obtain a methylsulfonyl compound.

When it is desired that the final product contain a hydroxy substituted heterocyclic group, it is preferred that the starting heterocyclic amine contain the corresponding acyloxy or aralkyloxy groups. These may be prepared in the usual fashion by acylating the starting hydroxy heterocyclic compoound with acyl halide or anhydride in the presence of a tertiary amine or aralkylating with an aralkyl halide or sulfate. Of course the amine function would be protected in the customary manner. Hydrogenolysis of the aralkyl group to the desired hydroxy compound may then take place after the formation of the amidinourea. This may be accomplished with a metal catalyst (Pd/C, Pt etc.) in a polar medium (ethanol, THF, etc.) for example, sodium in liquid ammonia. Thus, for example, the 4-hydroxy-2-pyridyl amidinourea compound may be prepared from the corresponding 4-benzyloxy-2-pyridyl compound. The hydroxy compounds may also be prepared by hydrolysis of the acyl or aralykoxy compounds with acid.

When it is desired that the final product contain an N- or S-oxide of the group $R_1$, starting materials containing this function may be used or the final products may be oxidized using a peroxide, for example, an organic peracid, such as, m-chlorobenzoic acid.

Reactions may also be carried out at other stages of synthesis depending on the substituents present and the substituents desired and various combinations of the foregoing reactions will be determined by one skilled in the art in order that the desired product results. Thus, a phenylguanidine or amidinourea may be halogenated or nitrated as above, etc.

The following examples illustrate the preparation of the heterocyclic amidino substituted ureas of this invention and are not to be construed as a limitation thereof.

EXAMPLE I

The Preparation of 1-Propylcarbamoyl-3-(2-pyridylmethyl)guanidine dihydrochloride 1-(2-Pyridylmethyl)guanidine sulfate 2-Aminomethylpyridine (54.07 g) is added to a vigorously stirred solution of 2-methyl-2-thiopseudouronium sulfate (69.60 g) in 200 ml of H$_2$O. The stirred mixture is carefully warmed while being flushed with a continuous stream of N$_2$. Alkaline KMnO$_4$ is used to scavenge for evolved methyl mercaptan. The mixture is stirred at 65° C. over the weekend resulting in a bright yellow solution which is heated to boiling. After refluxing for 30 minutes the solution is filtered while hot and evaporated to dryness under reduced pressure. The residue is a brilliant green crystalline solid which is taken up in hot aqueous methanol. Upon cooling, crystals separate and the solid is collected and dried in vacuo yielding 65.6 g of crystals, MP 206°–207° C. The crystalline solid is taken up in boiling water; a portion of Darco G-60 is added and the mixture filtered. The filtrate is concentrated and cooled. The crystalline precipitate is collected, washed with methanol and dried, yielding 8.6 g of a white crystalline product, MP 208°–209° C. which is determined to be the desired 1-(2-pyridylmethyl)-guanidine sulfate.

1-(Propylcarbamoyl)-3-(2-pyridylmethyl)guanidine dihydrochloride 1-(2-Pyridylmethyl)guanidine sulfate (13.15 g) and 10 ml of CHCl$_3$ are added to a vigorously stirred solution of 50% aqueous NaOH (5.2 g) and THF (15 ml). The mixture is stirred at RT for 2 hours. A 5 gram portion of solid anhydrous Na$_2$SO$_4$ is added and the mixture is stirred at room temperature for an additional hour. 100 ml of CHCl$_3$ and 50 ml of CH$_3$CN are added to the vigorously stirred mixture followed by an additional 5 g portion of Na$_2$SO$_4$. A solution of N-propyl isocyanate (5.11 g) and 75 ml of THF is added dropwise to the mixture and stirred at RT overnight. The solvent is evaporated in vacuo and the dark residue is mixed with 200 ml of CHCl$_3$, 100 ml of saturated aqueous sodium chloride and 50 ml of water. The organic layer is separated and the aqueous layer is washed with an additional 200 ml portion of CHCl$_3$. The organic phases are combined, washed with 70 ml of aqueous sodium chloride containing 5 ml of 50% aqueous NaOH, dried, filtered and concentrated in vacuo. The concentrate is acidified with ethereal HCl and evaporated to dryness under reduced pressure. The residue is taken up in boiling methanol, treated with Darco G-60 and filtered. The filtrate is concentrated to approximately 200 ml on a hotplate and diluted with approximately 200 ml of acetonitrile with continued heating. The hot solution is allowed to cool and the resultant precipitate collected, washed with acetonitrile and absolute ethanol. The solid is suspended in 200 ml of warm absolute ethanol, filtered while hot and dried in vacuo at 55° C. overnight to give 6.90 g of a blue white solid, MP 216°–218° w/dec.

EXAMPLE II

The Preparation of 1-Carbamoyl-3-(4-pyridylmethyl)guanidine dihydrochloride

1-Cyano-3-(4-pyridylmethyl)-guanidine

4-Amino methyl pyridine (16.22 g) is added to a stirred suspension of N-cyano-O-(m-cresyl)pseudourea (27.51 g) in 200 ml of isopropanol. The mixture is heated to boiling and refluxed for five hours. The reaction mixture is filtered and the filtrate evaporated under reduced pressure. The residue is stirred in 250 ml of chloroform overnight, the solvent removed under reduced pressure, treated with 250 ml of diethyl ether, the ether decanted and the residual gum treated with 200 ml of 5% HCl and stirred at room temperature for one hour. The mixture is filtered, extracted twice with 200 ml portions of diethyl ether and cooled to about 5° C. The solution is treated carefully with a 50% aqueous sodium hydroxide solution to a pH of 9 and extracted twice with 250 ml portions of methylene chloride. The organic extracts are combined, dried, filtered and evaporated to dryness under reduced pressure leaving a small amount of colored liquid. The aqueous layer is saturated with sodium chloride and re-extracted. After drying, the extracts are evaporated under reduced pressure. The aqueous phase is concentrated under reduced pressure and diluted with ethanol. The precipitated salts are removed by filtration and the filtrate concentrated under reduced pressure. The residue is azeotroped with 150 ml of toluene. The residue is stirred with 250 ml of isopropanol, filtered and evaporated under reduced pressure. The residue is triturated with 250 ml of isopropanol and filtered. The filtrate is dried, filtered, and evaporated under reduced pressure. The residue is taken up in a methanol/ethyl acetate mixture and allowed to stand. After trituration, the mixture is stirred in water overnight, the precipitate then collected and dried in air. The off-white solid is recrystallized from water yielding 12.10 g of pale yellow crystals which are dried in vacuo (55° C.), MP 92°–93° C. IR and elemental analysis indicate the desired guanidine.

1-Carbamoyl-3-(4-pyridylmethyl)guanidine dihydrochloride

Concentrated HCl (21 ml) is added to a mixture of 1-cyano-3-(4-pyridylmethyl)guanidine (10.0 g) in 500 ml of isopropanol. A pale yellow precipitate forms. The stirred suspension is heated on a steam bath and boiled for ten minutes. The solvent is evaporated under reduced pressure and the residual solid treated with 25 ml of concentrated HCl. The solution is heated on a steam bath for several minutes and diluted with isopropanol (50 ml) and allowed to cool. The resulting solid is collected and dred in air, extracted into 900 ml of methanol, which is filtered, and concentrated on a not plate. The hot solution is diluted with ethyl acetate and concentrated further. A white precipitate forms on cooling which is collected and dried in air giving the desired amidinourea dihydrochloride, MP 208°–209.5° C. w/dec.

EXAMPLE III

The Preparation of 1-Propylcarbamoyl-3-(2-[2-pyridyl]ethyl)guanidine 2-(2-Guanidino ethyl)pyridine 2-(2-Aminoethyl)pyridine (50.0 g) is added to a vigorously stirred solution of 2-methyl-2-thiopseudouronium sulfate (57.07 g) in 165 ml of H$_2$O. The mixture is warmed slowly to boiling with a continuous flow of N$_2$ passed through the mixture. The evolved methyl sulfide is scavenged using alkaline potassium permanganate solution (25 g KMnO$_4$ in 250 ml of 10% aqueous sodium hydroxide). The solution is refluxed for one hour and then allowed to cool. The solid is stripped off under reduced pressure and the residue crystallizes on standing. The crystalline product is taken up in boiling 95% ethanol and filtered while hot. The hot solution is diluted with 100 ml of acetonitrile and filtered hot. The filtrate is boiled down and diluted with acetonitrile. After cooling, the white crystalline product is collected, washed with ethanol and acetonitrile and dried to yield 64.35 g of the desired guanidine sulfate, MP 111°–112° C. The crystalline solid is extracted with boiling absolute ethanol and the hot extract filtered through a Celite mat and concentrated. The white solid is collected and dried in vacuo, MP 152°–153° C.

1-Propylcarbamoyl-3-(2-[2-pyridyl]ethyl)guanidine

Anhydrous $Na_2SO_4$ (20 g) is added to a stirred mixture of 2-(2-guanidinoethyl)pyridine sulfate, and 50% aqueous NaOH (12.0 g) in 250 ml of THF and stirred at room temperature for four and one half hours. A solution of propyl isocyanate (12.77 g) and 250 ml of THF is added dropwise to the reaction mixture and stirred at room temperature. The solvent is evaporated under reduced pressure and the residue taken up in a mixture of $H_2O$ (250 ml) and methylene chloride (400 ml). After stirring at RT for 30 minutes, the organic phase is separated, and the aqueous layer extracted with methylene chloride (250 ml). The organic layers are combined, dried, filtered, and evaporated to near dryness under reduced pressure. Prior to evaporation the solution is filtered to remove small amounts of particulate material and then evaporated to dryness under reduced pressure. The residue is treated with methanolic hydrogen bromide and the solution evaporated to dryness under reduced pressure. The residual solid is crystallized from acetonitrile, collected, washed with acetonitrile and dried in air to yield 40.6 g of the dihydrobromide salt of the desired guanidine, M.P. 144°–145° C. w/dec.

EXAMPLE IV

The Preparation of
1-(Propylcarbamoyl)-3-(4-pyridylmethyl)guanidine succinate

Anhydrous $Na_2SO_4$ is added to a stirred mixture of 1-(4-pyridylmethyl)guanidine carbonate monohydrate (12.0 g) and 50% aqueous NaOH (5.12 g) in 75 ml of DMSO which has been stirred at RT for five hours. The mixture is stirred at room temperature for an additional hour and then a solution of propyl isocyanate (5.11 g) in 25 ml of THF is added dropwise. The mixture is stirred at RT over the weekend, after which the THF is removed under reduced pressure. The residue is poured into 500 ml of $H_2O$ and the solution extracted twice with 300 ml portions of chloroform. The extracts are combined and dried, washed with 150 ml of saturated aqueous sodium chloride diluted with 100 ml of $H_2O$. The organic phase is separated, dried, filtered and evaporated in vacuo to yield a yellow liquid which is taken up in ethyl acetate and treated with ethereal HCl. The solvent is stripped off under reduced pressure and the residue is taken up in hot ethyl acetate containing a small amount of methanol. The solution is diluted with ethyl acetate, concentrated on a steam bath and cooled. A precipitate is collected and dried in vacuo to yield 4.35 g of a yellow solid which is crystallized from methanol/acetonitrile and dried to give a pale yellow powder, MP 174°–176° C., which is confirmed to be the desired 4-pyridyl guanidine dihydrochloride salt.

The dihydrochloride salt is dissolved in saturated aqueous sodium chloride, the pH adjusted to 10 with 50% aqueous sodium hydroxide solution and the resulting suspension extracted three times with chloroform. The extracts are combined, dried, filtered and evaporated to dryness under reduced pressure. The residual yellow oil is combined with succinic acid and the mixture dissolved in a minimum volume of boiling isopropanol and allowed to stand in the cold. A white crystalline solid is collected, washed with isopropanol and dried in vacuo overnight. The material is recrystallized from acetonitrile/methanol and dried in vacuo to give 74% of the succinate salt as a white solid, MP 159°–160° C.

EXAMPLE V

The Preparation of
1-[3-(2-Pyridyl)propyl]-3-(propylcarbamoyl)guanidine dihydrochloride 3-(2-Pyridyl)propyl guanidine A mixture of 3-(2-pyridyl)propylamine (13.55 g) and 2-methyl-2-thiopseudourea sulfate (13.85 g) in 40 ml of $H_2O$ is stirred under reflux for one hour and then at RT for three days. Aqueous sodium hypochlorite solution is used to scavenge for evolved methyl mercaptan. The solution is filtered, diluted with a small volume of ethanol and concentrated under reduced pressure. The white solid residue is extracted into boiling aqueous ethanol, the solution is filtered while hot and allowed to cool. The white solid is collected, washed with ethanol and dried in air. The white solid is extracted with one liter of boiling 95% ethanol. The filtrate from the isolation of the solid is stripped to dryness under reduced pressure and the resulting residue is taken up in 95% ethanol and added to the above extract. The mixture is filtered to yield a white solid, MP 225°–227° w/dec. The filtrate is concentrated under reduced pressure and the resulting residue taken up with 95% ethanol containing acetonitrile. The solvent is evaporated in vacuo and the residue is taken up in boiling methanol, diluted with acetonitrile and allowed to stand at room temperature. The resulting solid is collected, washed with acetonitrile and ethanol and dried in air. This material contains unreacted starting material. This solid is treated with 20% nitric acid, diluted with ethanol, and concentrated in vacuo. The concentrate is diluted with 125 ml of absolute ethanol and cooled. The white precipitate is collected, washed thoroughly with absolute ethanol and dried in air to yield 4.4 g of the desired 3-(2-pyridyl)propyl guanidine dinitrate MP 172°–174° C.

The filtrate from above is evaporated and the residue treated with 20% aqueous nitric acid, diluted with approximately 10 volumes of ethanol and stirred at room temperature for 30 minutes. The solvent is removed in vacuo and the residue triturated in boiling absolute ethanol. The slurry is cooled and the solid collected, washed with absolute ethanol and dried in vacuo yielding 13.96 g of an off-white powder confirmed as the guanidine dinitrate MP 174°–178° C.

1-[3-(2-Pyridyl)propyl]-b 3-(propylcarbamoyl)guanidine dihydrochloride hydrate

A 50% aqueous sodium hydroxide solution (6.40 g) is added slowly to a suspension of 3-(2-pyridyl)propyl guanidine dinitrate (12.17 g) in 200 ml of THF followed by the addition of 200 ml of THF. The suspension is stirred vigorously at RT for 20 hours after which anhydrous $Na_2SO_4$ (25 g) is added to the mixture. Stirring is continued for one half hour after which a solution of propyl isocyanate (3.40 g) in 100 ml of THF is added dropwise to the mixture. The mixture is stirred at RT overnight. The solvent is stripped off under reduced pressure and the residue taken up in a mixture of methylene chloride (250 ml), $H_2O$ (150 ml) and saturated sodium chloride solution (150 ml). The organic phase is separated and the aqueous layer extracted with methylene chloride. The organic layers are combined, dried, filtered, and treated with methanolic HCl, and stripped to dryness under reduced pressure. The partially crystalline residue is stirred at room temperature for ten minutes in a mixture of H₂O (150 ml), 10% HCl (50 ml), and methylene chloride (100 ml). The organic layer is separated and discarded. The aqueous phase is adjusted to a pH of 7 with solid NaHCO$_3$ and extracted twice with methylene chloride. Extracts are combined, dried, filtered and concentrated under reduced pressure. The concentrate is acidified with etherial HCl after dilution with acetonitrile (100 ml) and then stripped dry under reduced pressure. The residue is taken up in boiling absolute ethanol, filtered hot through Celite, concentrated and diluted with a small volume of ethyl acetate and concentrated to a syrup. Trituration initiated crystallization of the syrup which is then diluted with about 1 volume of acetonitrile and then allowed to stand. The crystalline mass is broken up and collected, washed with cold acetonitrile, ethyl acetate solution (1:1) and dried in vacuo to yield 6.88 g of crystals MP 96°–98° C. of the dihydrochloride hydrate salt.

EXAMPLE VI

Preparation of 1-Methyl-3-(propylcarbamoyl)-1-(2-[2-pyridyl]ethyl)-guanidine dihydrochloride A mixture of 1-methyl-1-(2-[2-pyridyl]ethyl)guanidine sulfate hemi-hydrate (16.23 g) and 50% aqueous sodium hydroxide (5.60 g) in 300 ml of THF is stirred at room temperature for one and one half hours after which anhydrous Na$_2$SO$_4$ (25 g) is added to the mixture. The mixture is stirred at RT for one hour after which a solution of propyl isocyanate (5.96 g) in 100 ml of methylene chloride is added dropwise. The mixture is stirred at RT overnight. The solvent is removed under reduced pressure and the residue taken up in a mixture of H$_2$O (100 ml) and methylene chloride (500 ml). The mixture is shaken several minutes after which the organic layer is separated. The aqueous layer is washed with methylene chloride (250 ml) and the organic layers are combined, dried, filtered and concentrated under reduced pressure. The concentrate is treated with etheral HCl and stripped to dryness. The residue is crystallized from acetonitrile/methanol and the product collected, washed with acetonitrile, and dried in vacuo to yield 10.21 g of a white solid confirmed to be the 1-methyl-3-propyl carbamoyl guanidine dihydrochloride. MP 200°–201° C. The concentration of the filtrate afforded 8.30 g of a second crop of white crystals, MP 194°–196° C.

EXAMPLE VII

The Preparation 1-Carbamoyl-3-(2-pyridylmethyl)guanidine dihydrochloride

1-Cyano-3-(2-pyridylmethyl)guanidine

A mixture of 2-amino methyl pyridine (10.91 g) and 1-cyano-2-(3-tolyl)pseudourea (17.52 g) in 250 ml of isopropanol is stirred at reflux under a nitrogen atmosphere for 5 hours. The reaction mixture is allowed to cool to room temperature and the solvent is removed in vacuo. The dark green residual oil is stirred in 250 ml of diethyl ether. The resultant solid is collected and washed with ether, and ground to a paste in 100 ml of diethyl ether. The solid is filtered, washed with ether and dried in air. The solid is taken up in boiling acetone and filtered hot, concentrated in a hot plate and cooled. The precipitate is collected and recrystallized from acetone to yield 7.08 g of the cyano guanidine, MP 144° C.

1-Carbamoyl-3-(2-pyridylmethyl)guanidine dihydrochloride

Concentrated HCl (15.4 ml) is added to a stirred solution of 1-cyano-3-(2-pyridylmethyl)guanidine (4.50 g) in 310 ml of isopropanol. The reaction mixture is stirred at room temperature overnight. The solvent is concentrated in vacuo and the residue treated with 1.8 liters of boiling ethanol. The resulting suspension is stirred and heated while adding small portions of water until most of the solid has dissolved. The solution is filtered through Celite, diluted to 2 liters with absolute ethanol and concentrated on a hot plate and cooled. The first crop of crystals, MP 214°–215° C. w/dec, and the second crop of crystals, MP 215°–216° C. w/dec, obtained by concentration of the filtrate, were combined to give 2.60 g of the carbamoyl guanidine as a grey-green solid. The grey-green solid is dissolved in boiling ethanol, treated with Darco G-60 and filtered. The filtrate is boiled down on a hotplate and the white crystalline precipitate is collected, washed with absolute ethanol and dried in air yielding 1.77 g of the desired product MP 214°–216° C. w/dec.

This invention further encompasses a novel method for the treatment of human and veterinary spasmolytic disorders, arrhythmic conditions, hypertensive conditions, gastrointestinal disorders and protozoal infestations by the administration of a compound of the Formulae I–VII.

The compounds of this invention have a useful degree of gastric antisecretory activity and are effective in reducing the volume and the acidity of the gastric fluid in humans and mammals. Further, these compounds produce a considerable spasmolytic action on the gastrointestinal musculature, i.e., they reduce the peristaltic action of the gastrointestinal musculature which is manifested by a delay in gastric emptying time. It should further be noted that these compounds are also characterized by their low acute oral toxicity.

In particular, the heterocyclic amidino substituted ureas as herein described are useful in the treatment of such gastrointestinal disorders and diseases as duodenal ulcer and peptic ulcer. The compounds of this invention are also useful as antidiarrheal agents.

The instant compounds may be used alone or in combination with other known antacids such as aluminum hydroxide, magnesium hydroxide, magnesium trisilicate, aluminum glycinate, calcium carbonate and the like.

The compounds of this invention possess blood-pressure-lowering activities and are also useful as antihypertensive agents.

The compounds described herein also possess useful anti-arrhythmic properties as well as useful local anesthetic properties.

Various tests in animals have been carried out to show the ability of the compounds of this invention to exhibit reactions that can be correlated with activity in humans. These tests involve such factors as the effect of the heterocyclic amidino substituted ureas on gastric secretion, their spasmolytic effect, their blood-pressure-lowering effect, and determination of their toxicity. It has been found that the compounds of this invention, when tested in the above variety of situations, show a marked activity.

One such test is the gastric secretion test. This test is carried out as follows: Shay rats are fasted for 4–8 hours and water is given ad lib. The rats are selected at random and separated into groups of ten. The animals are treated intraduodenally (I.D.) with the test compound or the vehicle immediately subsequent to the ligation of the stomach at the pyloric sphincter. The animals are sacrificed with chloroform at four hours post-drug-administration, the stomach removed and its contents assayed for volume, pH and total acids.

A second gastric secretion test is carried out on the dog. This is outlined in the *Handbook of Physiology*, Section 6: Alimentary Canal, Volume II: Secretion; American Physiology Society, Washington, D.C., 1967.

It has been found that the compounds of this invention, when subjected to the above gastric secretion tests, display marked ability to decrease gastric volume and gastric acidity. These tests are known to correlate well with gastric activity in humans and are standard tests used to determine antisecretory properties.

To determine the anti-ulcer effectiveness, the following test is employed: Male Wistar rats (130-150 grams) are fasted for 24 hours, then given reserpine at 5 mg/kg i.p. Twenty-four hours later, the stomachs are removed and examined for ulceration. Ulcers are graded on a 0-4 scale and the number of ulcers are recorded.

Determination of antispasmolytic properties can be carried out by the procedure outlined by D. A. Brodie and S. K. Kundrats in their article entitled "Effect of Drugs on Gastric Emptying in Rats," *Fed. Proc.* 24:714 (1965). Acute toxicity is calculated according to the standard Licthfield-Wilcoxon procedure.

Various tests can be carried out in animal models to show the ability of the compounds of this invention to exhibit reactions that can be correlated with antidiarrheal activity in humans. The following tests are considered to be standard tests used to determine antidiarrheal properties. This correlation can be shown by the activities of compounds known to be clinically active.

1. Fecal output in rat: The oral $ED_{50}$ (that dose which would be expected to reduce fecal output by 50%) is determined by a method described by Bass et al., 1972. Briefly, the method involves dosing the rats and collecting the fecal output over an 8-hour period (4 P.M.-midnight) with the room darkened starting at 4:30 P.M.

Ref: Bass, P., Kennedy, J. A. and Willy, J. N.: Measurement of fecal output in rats. *Am. J. Dig. Dis.* 10:925-928, 1972.

2. Castor oil test in mice: Groups of mice are orally dosed with test compound and a half hour later all mice are given 0.3 ml of castor oil. Three hours after castor oil administration, all mice are checked for diarrhea and the dose of testing compound which protected 50% of the mice from diarrhea is the $ED_{50}$ dose; 3. Castor oil test in rats: The test is conducted according to Niermegeers et al., 1972. The rat orally dosed with graded doses of test compound. One hour after dosing, each animal is challenged with 1 ml of castor oil orally. Fecal output is examined 1, 2, 3, 4, 6 and 8 hours after castor oil. Absence of diarrhea is the criterion of drug effectiveness.

Ref: Neimegeers, C. J. E., Lenaerts, F. M. and Janssen, P. A. J. Difenoxine, a potent, orally active and safe antidiarrheal agent in rats. *Arzneim-Forschung* (Drug Res.) 22, 516-518, 1972.

Tests in animals have also been carried out to show the ability of compounds of this invention to exhibit activity that can be correlated with antihypertensive action in humans. One such test is outlined by Jacques de Champlain, Lawrence R. Krahoff and Julius Axelrod in *Circulation Research* XXIII:479 (1968). This testing method is known to correlate well with antihypertensive activity in humans and is a standard test used to determine antihypertensive properties. In view of the results of this test, the heterocyclic substituted amidino ureas of this invention can be considered to be active antihypertensive agents.

The heterocyclic substituted amidino ureas and thioureas of this invention are useful in the treatment of parasitic infestations of a human host, particularly parasitic protozoal infestations.

The heterocyclic substituted amidino ureas are also useful in the veterinary treatment of blood-residing parasitic diseases afflicting cattle, horses, sheep, pigs, dogs, chickens, turkeys and geese.

These compounds are useful in the treatment of veterinary diseases caused by parasitic helminths, particularly Filaria, and by parasitic protozoa, particularly Plasmodium and Babesia.

Microbiological tests can be carried out in model systems to show the ability of the heterocyclic substituted amidino ureas of this invention to exhibit activity that can be correlated with antiprotozoal activity in humans and animals. The following microbiological test can show the ability of the compounds of this invention to inhibit parasitic protozoal growth and reproduction.

ANTIMALARIAL BLOOD SMEAR TEST

Mice are injected intraperitoneally with 5,000,000 parasitized blood cells from a donor. Groups of ten mice receive inoculations administered subcutaneously in doses ranging from 0.15 to 100 mg/kg, suspended in 0.5% methecel solution (doses expressed as base). The compound of interest is repeatedly injected on the day of inoculation (Day 1), Day 2 and Day 3. Blood smears are performed on Days 4, 5, 6 and 10 and the number of parasitic protozoa noted.

The compositions of the present invention can be prepared in forms suitable for administration by compounding an effective single dose amount of a compound of Formula I above, with known ingredients generally employed in the preparation of therapeutic compositions provided as tablets, capsules, lozenges, pills, powders, granules, suspensions, oil and water, or water and oil emulsions of similar forms which can be taken orally. The treatment of animals can be accomplished by incorporating an effective amount of a compound of Formula I in the animal diet with feed supplement or dissolved in the animal's fluid intake.

The compounds are readily absorbed into the blood stream from the stomach and intestines when taken orally. The preferred method of treatment is, therefore, to give the drug orally which is also the safest and most practical route of administration. Optional modes can be used where, for example, the human or animal is not eating or cannot swallow or has difficulty in swallowing, other methods of administration which permit the drug to be absorbed in the gastrointestinal tract or which deliver a solution of the drug directly to the blood stream can be employed.

The method of administration may also vary depending on the purpose of administration. For example, use as a prophylaxis or preventive treatment, a pre-immunity suppressant or as treatment of infected animals can require different methods of treatment and dosage forms.

The dosage regimens in carrying out the methods of this invention are those which insure maximum therapeutic response, bearing in mind, of course, that in selecting the appropriate dosage in any specific case, consideration must be given to the patient's weight, general health, age, the severity of the disorder, and other factors which may influence response to the drug. The average effective dose is between about 0.1 to about 50 mg. per kg. of body weight with about 1.0 to about 10 mg/kg being preferred.

Further, the active heterocyclic amidino substituted urea may be administered alone or in admixture with other agents having the same or different pharmacological properties.

The following are detailed examples which show veterinary and pharmaceutical compositions containing the active compounds of Formula I and serve to illustrate the preparation thereof:

EXAMPLE VIII 25 g of 1-[3-(2-Pyridyl)propyl]-3-(propylcarbamoyl)-quanidine dihyrochloride 175 g of peanut oil are intimately mixed with each other. Portions of 200 mg. each of said mixture are filled into soft gelatin capsules thus containing 25 mg of the active compound. The capsules are suitable for administration to humans and small animals for prophylactic or treatment of blood residing parasite diseases including malaria and heart worm.

EXAMPLE IX

Ten thousand tablets for oral use, each containing 50 mg are prepared from the following types and amounts of material:

| Ingredients | Grams |
| --- | --- |
| 1-Methyl-3-(propylcarbamoyl)-1-(2-[pyridyl]ethyl) guanidine dihydrochloride) | 500 |
| Lactose U.S.P. | 350 |
| Potato Starch U.S.P. | 346 |

The mixture is moistened with an alcoholic solution of 20 grams of stearic acid and granulated through a sieve. The granulated material is added to the following mixture.

| Ingredient | Grams |
| --- | --- |
| Potato Starch U.S.P. | 320 |
| Talcum | 400 |
| Magnesium Stearate | 500 |
| Lactose | 64 |

The mixture is thoroughly mixed and compressed into tablets. The tablets are especially useful for human use.

EXAMPLE X

An elixir in which each 5 ml contains 50 mg of 1-Carbamoyl-3-(2-pyridylmethyl)guanidine dihydrochloride is prepared by diluting 750 ml of invert sugar with 100 ml of water and adding to this 0.3 g of benzoic acid and 10 g of 1-Propylcarbamoyl-3-(2-[2-pyridyl]ethyl)guanidine dihydrobromide hydrate. 100 ml of alcohol (U.S.P. containing 0.2 g of flavors) is added and water is added to a total volume of 1 liter. The solution is thoroughly mixed, filtered and bottled. The preparation is useful for administering to humans, small animals and avian species for prophylactic treatment in combatting helmenthic diseases.

EXAMPLE XI

Capsules are prepared as follows:
150 g of 1-(Propylcarbamoyl)-3-(4-pyridylmethyl)-guanidine succinate
3 g magnesium stearate
2 g of finely divided silica sold under the trademark CAB-O-SIL by Godfrey L. Cabot, Inc., Boston, Mass., and
234 g of lactose.

The ingredients are thoroughly mixed with each other and the mixture is filled in gelatin capsules. Each capsule contains 500 mg of the composition and thus 150 mg of the succinate salt. The capsules can be administered to humans or small animals.

EXAMPLE XII

Tablets are prepared as follows:
100 g of 1-[3-(2-Pyridyl)propyl]-3-(propylcarbamoyl)-guanidine dihydrochloride hydrate
20 g of corn starch
14 g of calcium carbonate, and
1 g of magnesium stearate.

The active compound and starch are thoroughly mixed, moistened with a 10 percent gelatin solution, and granulated by pressing through a No. 20 sieve. The granules are dried, thoroughly mixed with calcium carbonate and magnesium stearate, and compressed into tablets, each weighing about 125 mg and containing 100 mg. The tablets are suitable for administration to humans and small animals.

EXAMPLE XIII

Composition:
75 g of 1-(Propylcarbamoyl)-3-(2-pyridylmethyl)guanidine dihydrochloride
50 g of microcrystalline cellulose,
10 g of polyvinylpyrrolidine,
5 g of magnesium stearate, and
85 g of starch.

The active compound and cellulose are intimately mixed, moistened with a polyvinylpyrrolidine solution in water, and granulated by pressing through a No. 10 sieve. The dried granules are mixed with starch and magnesium stearate and are compressed to dragee cores, each weighing 225 mg. The cores are now provided with an elastic subcoat of an aqueous sugar solution containing 60 g of powdered acacia, 60 g of powdered gelatin, and 600 g of sugar per liter of solution. Thereafter a dusting powder mixture of 180 g of powdered sugar, 60 g of powdered starch, 1 g of powdered talc, and 1 g of powdered acacia is applied to the dragee cores. Coating with the gelatin subcoat and dusting are repeated above five times. The thus treated cores are sugar coated in the coating pan with a 60 percent sugar solution. Sugar coating is repeated until each dragee weighs about 400 mg. The preparation is suitable for administration to humans and small animals.

EXAMPLE XIV

This example illustrates the utilization of a representative member of the compounds of the present invention as an antimalarial agent in an animal feed. In a manner similar to that described below, the remaining compounds encompassed by the present invention may also be incorporated as active antimalarial agents into animal feeds.

A medicated poultry feed intended as a starter feed for boilers is prepared by blending 0.005 percent by weight of 1-(2,6-dimethylphenylcarbamoyl)-3-(2-pyridylmethyl)guanidine in a basic poultry ration consisting of:

| Ingredient | Amount |
| --- | --- |
| Corn meal, No. 2 yellow, ground, gms | 1123 |
| Stabilized grease or vegetable oil, gms | 60 |
| Soybean oil meal (low fiber content 50% protein) gms | 480 |
| Corn Gluten meal, gms | 50 |
| Fish meal, antioxidant treated, 60% protein, gms | 30 |
| Fish solubles, dried basis, gms | 10 |
| Meat and bone scraps, 50% protein, gms | 140 |
| Corn distillers dried solubles, gms | 50 |
| Alfalfa meal, 17% protein 100,000 A/lb. | 30 |
| Salt iodized, gms | 5 |
| Manganese sulfate, feed grade, gm | 0.75 |
| Zinc carbonate or oxide, gm | 0.25 |
| Riboflavin, gms | 3 |
| Vitamin $B_{12}$, mgs | 6 |
| Calcium pantotheante, gms | 5 |
| Niacin, gms | 30 |
| Stabilized vitamin A USP units | 6,000,000 |
| Vitamin $D_3$, IC units | 650,000 |
| Vitamin E acetate, IU | 5,000 |
| Vitamin E (menadione sodium bisulfite) gms | 2 |
| DL-methionine or hydroxy analog, lb. | 1 |
| Antioxidant (ethoxyquin or butylated hydroxy toluene), lb. | 0.25 |

Similar feeds can be prepared containing any of the active amidinourea compounds of Formula I.

EXAMPLE XV

Encapsulates of 1-Carbamoyl-3-(4-pyridylmethyl)-guanidine dihydrochloride are prepared by the procedure of U.S. Pat. No. 3,773,919 as follows: poly-L-lactide 10.0 g and 1.0 g 1-Carbamoyl-3-(4-pyridylmethyl)-guanidine dihydrochloride were mixed and warmed to the melting point of the lactide. The mixture was cooled and ground into powder.

EXAMPLE XVI

Encapsulates of 1-[3-(2-Pyridyl)propyl]-3-(propylcarbamoyl)guanidine dihydrochloride hydrate are prepared following the procedure of U.S. Pat. No. 3,523,906 as follows: 5 g of the polycarbonate of 2,2-bis(4-hydroxyphenyl)-propane are dissolved in 50 cc of methylene chloride to prepare a solution. In this solution is dispersed 1 g of salimomycin. This solution is emulsified to fine droplets in 150 ml of ethylene gylcol and the methylene chloride gradually evaporated. The solid microcapsules are collected by centrifuge and rinsed with water.

As stated hereinabove, the implants in the form of encapsulates release the amidinourea compound in an amount such that the blood contains 10–20 nanogram %. As shown in the Examples, various types of encapsulates may be used, all of which may have varying rates of release of the compound and, when taken with the variation in sizes of animals, it can be readily realized that varying sizes of implants, will be required depending on the situation. In general, however, the size of the implant will vary from about 0.5 to about 4 grams and, if necessary, multiple dosage forms may be administered to large animals such as cattle. The amount of amidinourea in the implant may vary from about 5 to 95 wt.%. Encapsulates may be inserted through a slit in the skin or in the case of microcapsules, administered by injection equipment.

We claim:

1. A method for the treatment of protozoal infections in afflicted humans or animals which comprises administering thereto an effective amount of a compound of the formula

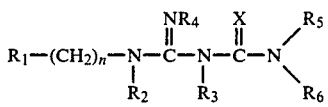

wherein:
X is O or S;
n is 0 to 3;
$R_1$ is a 5, 6 or 7 atom ring including 1 to 3 hetero atoms of N, O or S, or 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, or carbazole, which may be substituted by lower alkyl, lower alkenyl, phenyl, substituted phenyl, lower alkynyl, phenyl lower alkyl, substituted phenyl lower alkyl, halo, nitro, cyano, sulfonyl, hydroxyl, carboxyl, lower alkanoyl, lower alkoxy, phenyl lower alkoxy, substituted phenyl lower alkoxy, halo lower alkoxy, amido, amino, lower alkylacyloxy, alkylamino, lower alkoxyamino, phenylalkoxyamino or substituted phenylalkoxyamino; or the N- or S-oxides thereof; provided $R_1$ is not pyridyl when n is 0;
$R_2$, $R_3$ and $R_4$ are hydrogen or lower alkyl;
$R_5$ and $R_6$ are hydrogen, lower alkyl, cycloloweralkyl, lower alkenyl, lower alkoxy, phenyl, substituted phenyl, phenyl lower alkyl, substituted phenyl lower alkyl or $R_5$ and $R_6$ together with the nitrogen to which they are attached form a 3 to 7 atom ring which includes 0 to 2 additional hetero atoms of N, O or S;
wherein substituted phenyl means a phenyl group substituted by halo, lower alkyl, halo loweralkyl, nitro, amino, loweralkanoylamino, hydroxyl, loweralkoxy, phenylloweralkoxy, loweralkylacyloxy, cyano, halo loweralkoxy or loweralkyl sulfonyl;
or a pharmaceutically acceptable salt thereof.

2. A method according to claim 1, wherein:
X is O or S;
n is 0, 1, 2 or 3;
$R_1$ is a substituted or unsubstituted 5, 6 or 7 atom ring including 1 to 3 hetero atoms of N, O or S; and N- and S-oxides thereof; provided $R_1$ is not pyridyl when n is 0;
$R_2$ is hydrogen or lower alkyl;
$R_5$ and $R_6$ are hydrogen, lower alkyl, cycloloweralkyl, lower alkoxy, phenylloweralkyl or substituted phenyl loweralkyl, or $R_5$ and $R_6$ together with the nitrogen to which they are attached form a 3 to 7 atom heterocycle;
or a pharmaceutically acceptable salt thereof.

3. A method according to claim 1 wherein $R_1$ is a heterocycle selected from the group consisting of 1-pyrrole, 2-pyrrole, 3-pyrrole, 2-furan, 3-furan, 2-thiophene, 3-thiophene, 2-tetrahydrothiophene, 3-tetrahydrothiophene, 1-imidazole, 2-imidazole, 4-imidazole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 1-(3-pyrroline), 2-(3-pyrroline), 3-(3-pyrroline), 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, and carbazole; where said heterocycle may be mono-, di-, tri- or tetra-substituted by lower alkyl, lower alkenyl, phenyl, substituted phenyl, lower alkynyl, phenyl lower alkyl, substituted phenyl lower alkyl, halo, nitro, cyano, sulfonyl, hydroxyl, carboxyl, lower alkanoyl, lower alkoxy, phenyl lower alkoxy, substituted phenyl lower alkoxy, halo lower alkoxy, amido, amino, lower alkylacyloxy, alkylamino, lower alkoxyamino, phenylalkoxyamino or substituted phenylalkoxyamino.

4. An animal feed additive comprising an effective anti-protozoal amount of a compound defined in claim 3 and an edible carrier material.

* * * * *